United States Patent
Elliott et al.

(10) Patent No.: US 7,892,816 B2
(45) Date of Patent: Feb. 22, 2011

(54) ELECTROCHEMICAL DETECTION OF SUBSTRATES

(75) Inventors: C. Michael Elliott, Fort Collins, CO (US); Carlo Alberto Bignozzi, Ferrara (IT); Di Xue, Fort Collins, CO (US); David W. Grainger, Salt Lake City, UT (US); Stefano Caramori, Ferrara (IT); Valeria Dissette, Rovigo (IT)

(73) Assignee: Colorado State University Research Foundation, Fort Collins, CO (US)

( * ) Notice: Subject to any disclaimer, the term of this patent is extended or adjusted under 35 U.S.C. 154(b) by 334 days.

(21) Appl. No.: 11/536,478

(22) Filed: Sep. 28, 2006

(65) Prior Publication Data

US 2008/0081329 A1    Apr. 3, 2008

(51) Int. Cl.
*C12M 1/34* (2006.01)
*C12M 3/00* (2006.01)

(52) U.S. Cl. .............. 435/287.2; 435/7.1; 435/283.1; 435/287.1; 435/288.3; 436/518; 436/524; 436/525; 422/50; 422/82.01

(58) Field of Classification Search ............ 435/7.1, 435/283.1, 287.1, 287.2, 288.3; 436/518, 436/524, 525; 422/50, 82.01
See application file for complete search history.

(56) References Cited

U.S. PATENT DOCUMENTS

| | | | | |
|---|---|---|---|---|
| 5,968,745 | A * | 10/1999 | Thorp et al. | 435/6 |
| 6,248,229 | B1 * | 6/2001 | Meade | 205/777.5 |
| 6,346,387 | B1 * | 2/2002 | Stewart et al. | 435/6 |
| 6,391,558 | B1 * | 5/2002 | Henkens et al. | 435/6 |
| 7,049,068 | B2 * | 5/2006 | Thorp et al. | 435/6 |
| 2002/0012943 | A1 * | 1/2002 | Fowlkes et al. | 435/7.1 |
| 2005/0136550 | A1 * | 6/2005 | Yang et al. | 436/514 |
| 2005/0191651 | A1 * | 9/2005 | Franzen et al. | 435/6 |
| 2006/0025593 | A1 * | 2/2006 | Xie et al. | 546/2 |
| 2006/0292624 | A1 * | 12/2006 | Thorp et al. | 435/6 |

* cited by examiner

*Primary Examiner*—Melanie J Yu
(74) *Attorney, Agent, or Firm*—Don D. Cha; Hamilton DeSanctis & Cha, LLP

(57) ABSTRACT

The present invention provides a method for detecting probe-target substrate binding. In particular, the present invention provides a method for detecting a surface bound target complex by detecting the redox reaction of a redox transition metal complex that is catalyzed by a redox-catalyst complex.

17 Claims, 8 Drawing Sheets

SEQUENCE LISTING

<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: Oligonucleotide

<400> SEQUENCE: 1
ctgaacggta gcatcttgac                                                   20

<210> SEQ ID NO 2
<211> LENGTH: 21
<212> TYPE: DNA
<213> ORGANISM: Artificial
<220> FEATURE:
<223> OTHER INFORMATION: Oligonucleotide with Linker
<220> FEATURE:
<221> NAME/KEY: misc_feature
<222> LOCATION: (1)..(1)
<223> OTHER INFORMATION: aminohexyl linker

<400> SEQUENCE: 2
ngtcaagatg ctaccgttca g                                                 21

<210> SEQ ID NO 3
<211> LENGTH: 21
<212> TYPE: DNA
<213> ORGANISM: Artificial
<220> FEATURE:
<223> OTHER INFORMATION: Oligonucleotide with Linker
<220> FEATURE:
<221> NAME/KEY: misc_feature
<222> LOCATION: (1)..(1)
<223> OTHER INFORMATION: aminohexyl linker

<400> SEQUENCE: 3
nctgaacggt agcatcttga c                                                 21

ELECTROCHEMICAL DETECTION OF SUBSTRATES

STATEMENT REGARDING FEDERALLY FUNDED RESEARCH

The U.S. Government has a paid-up license in this invention and the right in limited circumstances to require the patent owner to license others on reasonable terms as provided for by the terms of Grant No. CHE-0139637 and CHE-0113112 awarded by the National Science Foundation and Grant No. EB-000726 awarded by the National Institute of c:\Program Files\EUDORA\Attach\Patent Appl-5.docHealth.

FIELD OF THE INVENTION

The present invention relates to the detection of probe-target substrate binding. In particular, the present invention relates to detecting a surface bound target complex by detecting the redox reaction of a redox transition metal complex that is catalyzed by a redox-catalyst complex.

BACKGROUND OF THE INVENTION

Nucleic acid analysis is frequently sought for diagnosis of disease, microbial contamination, forensics, biosecurity and basic research and development. These analyses often use surface capture methods to identify a soluble DNA or RNA target analyte by selective or specific, complementary complexation with a matching probe nucleic acid oligomer immobilized on a capture surface. One popular commercialized method—nucleic acid microarray analyses—use rapid robotic printing methods to place micrometer-sized spots of DNA target libraries onto activated solid supports in cataloged arrays. Exposure of these surfaces to samples containing unknown nucleic acid analytes permits simultaneous screening of up to tens of thousands of different complementary DNA or mRNA analytes or their single nucleotide polymorphisms (SNPs) in complex biological samples. While many modes of analyte detection of bound nucleic acid signal on the support are possible, measurement usually exploits image analysis of fluorescent emission from tags placed specifically on the captured analyte (typically using polymerase chain reaction). The fluorescent intensity of each microarray spot on the slide is then collected (via surface fluorescence scanning) and analyzed.

Fluorescence-based nucleotide microarray assays are technically attractive, currently the focus of a billion-dollar commercial effort, but exhibit significant limitations: (1) fluorescence has only relative correlation with natural DNA target abundance without absolute reference to actual target concentrations, (2) fluorescence is relatively insensitive, requiring either pre-purification or amplification of DNA target to achieve reasonable assay detection limits (picomolar), (3) probe printing and target dye-labeling processes are expensive and time consuming, and (4) detection requires highly sophisticated optical scanners, laser excitation sources and post-assay image processing. As one alternative, electrochemical DNA detection has received substantial attention due to its intrinsically rapid response, ease of handling, compatibility with miniaturization technology and relatively low cost. By combining electrochemistry with the selectivity or specificity of biological recognition processes, electrochemical biosensors occupy an important analytical position.

Electrochemically based DNA analysis based on nucleic acid hybridization are prepared by immobilizing single-stranded DNA (ssDNA) oligomer probe sequences on electrode surfaces and using electroactive indicators to measure hybridization events between immobilized probes and their complementary DNA (cDNA) target fragments. Such electrochemical assays can be classified into two categories depending on their signal transduction mode on the electrode. Direct signal transduction sensors rely on electro-oxidation of nucleotide guanine or adenine residues in DNA target chains hybridized to electrode surfaces. See, for example, Wang, et al., *Anal. Chim Acta*, 1998, 375, 197-2003. To amplify weak oxidative signals from guanine or adenine oxidation to improve detection limits, $Ru(bpy)_3^{2+}$ ion has been employed as a redox mediator, producing electrocatalytic oxidation. See, for example, Johnston, et al., *J. Am. Chem. Soc.*, 1995, 117, 8933-8938; and Gore, et al., *Anal Chem.*, 2003, 75, 6586-6592. One of the drawbacks of this sensor design is the inherent destruction of the electrode-captured DNA probe and target, preventing further measurement. Indirect detection of hybridization, on the other hand, exploits enzyme labels, or other redox mediators such as $Os(bpy)_3^{2+}$, $Co(phen)_3^{3+}$ and $Co(bpy)_3^{3+}$, or intercalating organic compounds including daunomycin, methylene blue or acridine orange. It is believed that these electroactive sensitizers, some of which are chosen for their stability and reversibility in redox reactions, interact with ssDNA probes and hybridized double stranded DNA (dsDNA) via electrostatic binding to DNA phosphate groups, hydrophobic binding to dsDNA's minor groove and/or intercalation (hydrophobic partitioning) into base pairs. In some of these cases, DNA target hybridization is detected by measuring the redox current generated by redox mediators associated with dsDNA on the electrode. For sensitive, accurate and reliable determination of DNA target hybridization, these redox species must interact more efficiently with dsDNA than with ssDNA targets.

Accordingly, there is a continuing need for redox species that can interact more efficiently with dsDNA than with ssDNA targets in order to provide more sensitive, accurate and reliable determination of DNA target hybridization.

SUMMARY OF THE INVENTION

One aspect of the invention provides a method for determining the presence or absence of a target substrate in a test sample comprising:
  providing an electrode comprising:
    a conductive surface, and
    a probe that is bound to the conductive surface and is capable of binding to a target substrate;
  contacting the conductive-surface bound probe with the test sample to form a surface bound target complex if the target substrate is present in the test sample, wherein the surface bound target complex further comprises a first redox complex;
  contacting the surface bound probe or the surface bound target complex, if present, with a fluid medium comprising a second redox complex, wherein one of the first or the second redox complex is a redox transition metal complex that is capable of undergoing an oxidation-reduction reaction and the other of the first or the second redox complex is a redox-catalyst complex that is capable of catalyzing the oxidation-reduction reaction of the redox transition metal complex, and wherein the surface bound probe or the surface bound target complex, if present, is contacted with the fluid medium under conditions such that the redox transition metal complex does not undergo any significant amount (typically 10% or less, often 5% or less, more often 1% or less, and most often 0.1% or less) of oxidation-reduction reaction in the absence of the redox-catalyst complex;

detecting the oxidation-reduction reaction of the redox transition metal complex that is at least in part catalyzed (typically substantially all, e.g., at least 80%, often at least 90%, more often at least 95% and most often at least 98%) by the redox-catalyst complex; and determining the presence or absence of the target substrate in the test sample from the detected oxidation-reduction reaction.

In some embodiments, the first redox complex is covalently attached to the target substrate.

In other embodiments, the electrode is contacted with the first redox complex after said step of contacting the conductive-surface bound probe with the test sample such that when the surface bound target complex is present, at least a portion of the first redox complex intercalates into the surface bound target complex.

Still in other embodiments, the first redox complex is the redox transition metal complex that is capable of undergoing an oxidation-reduction reaction and the second redox complex is the redox-catalyst complex that is capable of catalyzing the oxidation-reduction reaction of the first transition metal complex.

Yet in other embodiments, the second redox complex is the redox transition metal complex that is capable of undergoing an oxidation-reduction reaction and the first redox complex is the redox-catalyst complex that is capable of catalyzing the oxidation-reduction reaction of the second transition metal complex.

Still in other embodiments, the first redox complex is a first transition metal complex.

In other embodiments, the second redox complex is a second transition metal complex.

Another aspect of the invention provides, a method for determining the presence or absence of a target substrate in a test sample comprising:

providing an electrode comprising:
a conductive surface, and
a probe that is bound to the conductive surface and is capable of binding to a target substrate;

contacting the conductive-surface bound probe with the test sample to form a surface bound target complex if the target substrate is present in the test sample, wherein the surface bound target complex further comprises a redox-catalyst complex that is capable of catalyzing the oxidation reduction reaction of a redox transition metal complex;

contacting the surface bound probe or the surface bound target complex, if present, with a fluid medium comprising the redox transition metal complex under conditions such that the redox transition metal complex does not undergo any substantial amount of oxidation-reduction reaction in the absence of the redox-catalyst complex;

detecting the oxidation-reduction reaction of the redox transition metal complex catalyzed by the redox-catalyst complex; and determining the presence or absence of the target substrate in the test sample from the detected oxidation-reduction reaction.

In some embodiments, the redox-catalyst complex is another transition metal complex.

Yet in other embodiments, the redox-catalyst complex is an organic redox-catalyst complex.

In some embodiments, said step of detecting the oxidation-reduction reaction comprises determining the current flow.

Yet in other embodiments, the redox-catalyst complex is covalently linked to the target substrate. Within these embodiments, in some instances the redox-catalyst complex is covalently linked to the target substrate through a linker moiety.

Still in other embodiments, the redox-catalyst complex is non-covalently bound to the surface bound target complex. Within these embodiments, in some instances at least a portion of the redox-catalyst complex is intercalated into the surface bound target complex.

In other embodiments, the probe and target substrate are oligonucleotides.

Still yet in other embodiments, one of the probe and target substrate is an antigen and the other is an antibody.

In other embodiments, one of the probe and target substrate is a ligand and the other is a receptor.

Still in other embodiments, the redox transition metal complex undergoes oxidation in the presence of the redox-catalyst complex.

Yet in other embodiments, the redox transition metal complex undergoes reduction in the presence of the redox-catalyst complex.

Still another aspect of the invention provides a method for detecting a non-linearly enhanced electro-generated signal using an electroactive sensing device comprising:

providing a redox-catalyst complex that is bound to a probe-target substrate complex, wherein the redox-catalyst complex is capable of catalyzing an oxidation-reduction reaction of a redox transition metal complex, and wherein the probe-target substrate complex is bound to the surface of an electrode;

contacting the redox-catalyst complex that is bound to the probe-target substrate complex with a fluid medium comprising the redox transition metal complex, wherein the oxidation-reduction reaction of the redox transition metal complex is catalyzed by the redox-catalyst complex; and detecting the non-linearly enhanced electro-generated signal using the electroactive sensing device.

In one embodiment, the redox-catalyst complex is non-covalently bound to the probe-target substrate complex.

Still in other embodiments, the redox-catalyst complex is covalently bound to the probe-target substrate complex.

Yet in other embodiments, the electroactive sensing device measures cyclic voltammetry.

In other embodiments, the electroactive sensing device measures differential pulse voltammetry.

In another embodiment, the redox-catalyst complex that is bound to the probe-target substrate complex catalyzes oxidation of the redox transition metal complex.

Still in other embodiments, the redox-catalyst complex that is bound to the probe-target substrate complex catalyzes reduction of the redox transition metal complex.

Still another aspect of the invention provides a method for determining the presence or absence of a target substrate in a sample comprising:

contacting the sample with an electrode comprising a surface bound probe to form a surface bound target complex, if a desired target substrate is present in the sample, wherein the surface bound target complex further comprises a first redox complex;

contacting the resulting electrode with a fluid medium comprising a second redox complex, wherein one of the first or the second redox complex is a redox transition metal complex that is capable of undergoing an oxidation-reduction reaction and the other of the first or the second redox complex is a redox-catalyst complex that is capable of catalyzing the oxidation-reduction reaction of the redox transition metal complex;

detecting the oxidation-reduction reaction of the redox transition metal complex catalyzed by the redox-catalyst complex; and determining the presence or absence of the target substrate in the sample from the detected oxidation-reduction reaction.

In some embodiments, the target substrate is a double stranded oligonucleotide. Within these embodiments, in some instances the probe further comprises a linker moiety that covalently links the probe to the electrode surface.

Still in other embodiments, the redox potential of the redox transition metal complex is about 800 mV or less relative to SCE.

Yet in other embodiments, the redox transition metal complex is of the formula:

$$[M(L)_p X_q]^m$$

wherein
m is an integer;
p is an integer from 1 to 6;
q is an integer from 0 to 5;
provided that the sum of p+q is such that M has no more than six binding sites;
M is a transition metal that can exist in at least two stable oxidation sates within the transition metal complex;
each X is a ligand independently selected from the group consisting of a halide, cyanide, pyridine and amine; and
each L is independently an optionally substituted aromatic ligand that comprises one, two or three coordinating atoms each of which is independently selected from the group consisting of nitrogen, oxygen, and phosphorous.

Within these embodiments, in some cases each L is independently selected from the group consisting of bipyridine, terpyridine, and phenanthroline, each of which is optionally substituted.

In other instances, M is Co.

Still in other instances, at least one of the aromatic ligand is substituted with a substituent having a steric bulk volume larger than a methyl group. In some particular cases, each of the aromatic ligand is independently selected from the group consisting of:

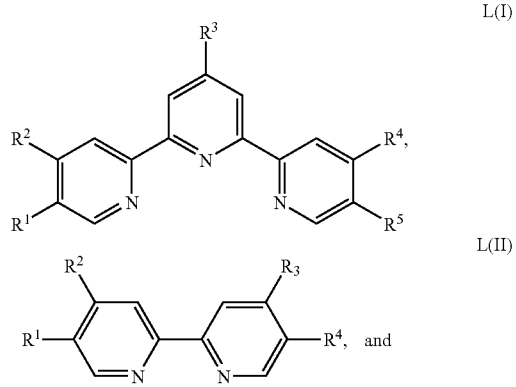

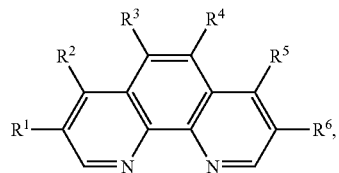

wherein
each of $R^1$, $R^2$, $R^3$, $R^4$, $R^5$, and $R^6$ is independently hydrogen, alkyl, cycloalkyl, aryl, aralkyl, an ester moiety of the formula —$CO_2R^7$, an amide moiety of the formula —$CONR^8R^9$;
$R^7$ is alkyl, cycloalkyl, aryl, or aralkyl; and
each of $R^8$ and $R^9$ is independently hydrogen, alkyl, cycloalkyl, aryl, or aralkyl;
provided at least one of $R^1$, $R^2$, $R^3$, $R^4$, or $R^5$ in L(I), or at least one of $R^1$, $R^2$, $R^3$, or $R^4$ in L(II), or at least one of $R^1$, $R^2$, $R^3$, $R^4$, $R^5$, or $R^6$ in L(III) is a substituent having a steric bulk volume larger than a methyl group.

In some instances, the redox transition metal complex is of the formula: $[M(L(I))_2]^{+m}$, $[M(L(II))_3]^{+m}$, or $[M(L(III))_3]^{+m}$.

Still in other embodiments, the surface bound probe further comprises a redox-catalyst complex that is capable of catalyzing the redox reaction of the redox transition metal complex. Within these embodiments, the redox-catalyst complex is of the formula:

$$[M^1(L^1)_a(X^1)_b]^n$$

wherein
n is an integer;
a is an integer from 1 to 6;
b is an integer from 0 to 5;
provided that the sum of a+b is such that $M^1$ has no more than six binding sites;
$M^1$ is a transition metal that can exist in at least two stable oxidation sates within the transition metal complex;
each $X^1$ is a ligand independently selected from the group consisting of a halide, cyanide, pyridine and amine; and
each $L^1$ is independently an optionally substituted aromatic ligand that comprises one, two or three coordinating atoms each of which is independently selected from the group consisting of nitrogen, oxygen, and phosphorous, and wherein at least one of the aromatic ligand comprises a linker that is attached to a binding moiety that is capable of binding to a double stranded oligonucleotide.

In other embodiments, the redox-catalyst complex is non-transitional metal complex such as organic redox-catalyst complex.

In some instances, $M^1$ is Ru, Fe, or Os.

Still in other instances, each $L^1$ is independently selected from the group consisting of dppz, dpphz, dmb, bpy, phen, and dpdphphz.

In one particular embodiment, the redox-catalyst complex is selected from the group consisting of $Ru(dppz)_2Cl_2$, $Ru(dmb)(dppz)Cl_2$, $Os(dppz)_2Cl_2$, $Os(bpy)(dppz)Cl_2$, $Os(dppz)(phen)Cl_2$, $Os(dpdphphz)(phen)Cl_2$, $[Os(phen)(dppz)(py)Cl]PF_6$, and $[Os(bpy)(dpdphphz)(py)Cl]PF_6$.

Another aspect of the invention provides a method for detecting oligonucleotide hybridization comprising:
contacting a fluid sample comprising an oligonucleotide with a substrate comprising a surface bound oligonucleotide probe such that the oligonucleotide sample and the oligonucleotide probe forms a hybridized oligonucleotide when the oligonucleotide sample and the oligonucleotide probe are sufficiently complementary to one another to form a hybrid pair, and wherein the hybridized oligonucleotide further comprises a first redox complex; and electrochemically analyzing the resulting substrate in a fluid medium comprising a second redox complex, wherein one of the first or the second redox complex is a redox transition metal complex that is capable of undergoing an oxidation-reduction reaction and the other of the first or the second redox complex is a redox-catalyst complex that is capable of catalyzing the oxidation-reduction reaction of the redox transition metal complex, and wherein the occurrence of the oxidation-reduction reaction of the redox transition metal complex is an indication of hybridization between the oligonucleotide sample and the oligonucleotide probe.

Still another aspect of the invention provides a kit for electrochemically detecting the presence of a probe-target substrate complex comprising:

(a)
 (i)
  (1) a substrate comprising:
   a conducting surface; and
   a probe having a sufficient selectivity or specificity for a desired target substrate such that when the desired target substrate is present the probe and the desired target substrate forms a surface bound target complex, wherein said probe is bound to said conducting surface; and
  (2) a first redox complex that is adapted to bind to the surface bound target complex; or
 (ii) a probe that is covalently linked to a first redox complex; and
(b) a second redox complex, wherein one of the first or the second redox complex is a redox transition metal complex that is capable of undergoing an oxidation-reduction reaction and the other is a redox-catalyst complex that is capable of catalyzing the oxidation-reduction reaction of the redox transition metal complex.

In one embodiment, the kit comprises:
(a)
 (1) said substrate comprising:
  the conducting surface; and
  the probe having a sufficient selectivity or specificity for the desired target substrate such that when the desired target substrate is present the probe and the desired target substrate forms the surface bound target complex, wherein said probe is bound to said conducting surface; and
 (2) said first redox complex that is adapted to bind to the surface bound target complex; and
(b) said second redox complex, wherein one of the first or the second redox complex is the redox transition metal complex and the other is the redox-catalyst complex.

Within this embodiment, in some instances the desired target substrate is in a fluid medium.

In other instances, said redox-catalyst complex binds non-covalently to the surface bound target complex. Within these instances, in some cases, at least a portion of said redox-catalyst complex intercalates into the surface bound target complex.

In other embodiments, said kit comprises:
(a) said probe that is covalently linked to a first redox complex; and
(b) said second redox complex, wherein one of the first or the second redox complex is the redox transition metal complex and the other is the redox-catalyst complex.

Within these embodiments, in some instances the desired target substrate is bound to the conducting surface.

DETAILED DESCRIPTION OF THE INVENTION

Definitions

Figure 1:
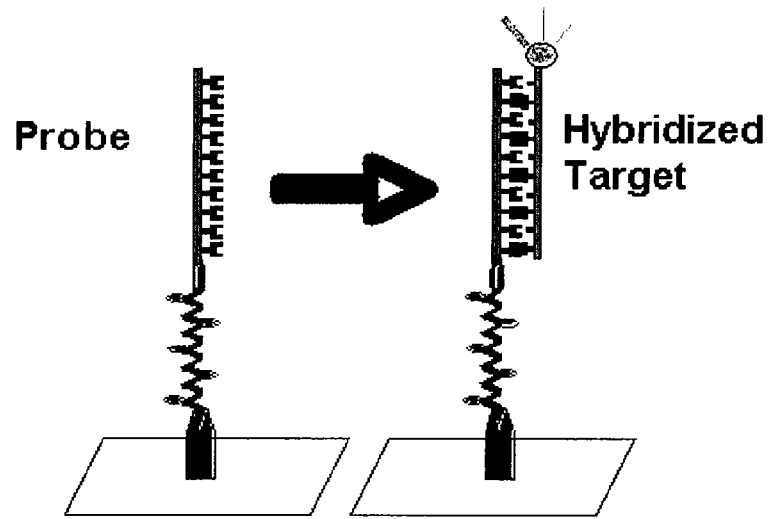
FIG. 1 is a schematic illustration of surface capture and detection by fluorescence of a soluble target nucleic acid complementary to an immobilized nucleic acid probe.

The expression "amplification of polynucleotides" includes methods such as polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., *PCR Protocols: A Guide to Methods and Applications*, 1990, Academic Press, San Diego; and Wu, D. Y. et al., *Genomics*, 1989, 4, 560-569. Reagents and hardware for conducting PCR are commercially available. Primers useful to amplify sequences from a particular gene region are preferably complementary to, and hybridize selectively or specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf, *Science*, 1986, 233, 1076.

The terms "substrate" and "receptor" refer to any combination of moieties that can selectively bind or interact with one another including, but not limited to, an oligonucleotide and its complementary oligonucleotide, an enzyme and a substrate that binds to the enzyme, a receptor and a ligand that binds to the receptor, an antibody binding to its antigen, an aptamer binding its target, etc. In one particular embodiment, the terms "substrate" and "receptor" refers to an oligonucleotide and the complementary oligonucleotide.

The term "redox transition metal complex" refers to a transition metal complex that is capable of undergoing reduction-oxidation (i.e., redox) reaction.

The terms "redox mediator" and "redox-catalyst complex" are used interchangeably herein and refer to a complex that catalyzes the redox reaction of a redox transition metal complex. The redox-catalyst complex can be another transition metal complex or an organic compound (i.e., organic redox-catalyst complex such as a redox-catalyst complex that does not contain a metal, such as transition metal).

The term "electrode" refers to an electric conductor that conducts a current in and out of an electrically conducting medium. The two electrodes, the anode and the cathode, receive and emit electrons, respectively. An electrode is used generally to describe the conductor. In the invention, an electrode can also be a microarray, consisting of a number of separately addressable electrodes, an ultramicroelectrode, or an ensemble of conducting particles or conducting carbon nanotubes, or a porous filtration frit.

The term "hybridized" refers to two nucleic acid strands associated with each other which may or may not be fully base-paired.

The term "intercalative moiety" and "intercalating agent" refers to planar aromatic or heteroaromatic moieties that are capable of partial insertion and/or stacking between the substrate and the receptor, e.g., adjacent base pairs of double-stranded oligonucleotides. These moieties may be small molecules or part of a larger entity, such as a protein.

The term "nucleoside" refers to a nitrogenous heterocyclic base linked to a pentose sugar, either a ribose, deoxyribose, or derivatives or analogs thereof. The term "nucleotide" relates to a phosphoric acid ester of a nucleoside comprising a nitrogenous heterocyclic base, a pentose sugar, and one or more phosphate or other backbone forming groups; it is the monomeric unit of an oligonucleotide. Nucleotide units may include the common bases such as guanine (G), adenine (A), cytosine (C), thymine (T), or derivatives thereof. The pentose sugar may be deoxyribose, ribose, or groups that substitute therefore.

The terms "nucleotide analog", "modified base", "base analog", or "modified nucleoside" refer to moieties that function similarly to their naturally occurring counterparts in terms of base paring and base stacking and complementary base-base recognition but have been structurally modified, for example, to resist degradation, or facilitate production, or provide alternative construction to the natural nucleotide biopolymer.

The terms "oligonucleotide" or "nucleotide sequence" refers to a plurality of joined nucleotide units formed in a specific sequence from naturally occurring heterocyclic bases and pentofuranosyl equivalent groups joined through phosphorodiester or other backbone forming groups to create polymers. This oligomeric construct can also have synthetic backbone modifications known to those skilled in the art to provide nucleotide polymers of diverse chemical linkages that still function in base paring, base stacking and double- and triple-strand formation.

The terms "oligonucleotide analogs" or "modified oligonucleotides" refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, which are known for use in the art.

The terms "redox-active moiety" or "redox-active species" refers to a compound that can be oxidized and/or reduced, i.e., which contains one or more chemical functions that accept and/or donate electrons.

"Alkyl" refers to a saturated linear monovalent hydrocarbon moiety of one to twelve, preferably one to six, carbon atoms or a saturated branched monovalent hydrocarbon moiety of three to twelve, preferably three to six, carbon atoms. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety of one to twelve, preferably one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like.

"Aryl" refers to a monovalent mono-, bi- or tricyclic aromatic moiety of 6 to 15 ring atoms which is optionally substituted with one or more, preferably one, two, or three substituents within the ring structure. When two or more substituents are present in an aryl group, each substituent is independently selected.

"Aralkyl" refers to a moiety of the formula —$R^b R^c$ where $R^b$ is an alkylene group and $R^c$ is an aryl group as defined herein. Exemplary aralkyl groups include, but are not limited to, benzyl, phenylethyl, 3-(3-chlorophenyl)-2-methylpentyl, and the like.

"Aromatic ligand" refers to an aryl moiety that comprises one or more ring heteroatom (i.e., heteroaryl moiety) that can coordinate with a transition metal "Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

"Cycloalkyl" refers to a non-aromatic, preferably saturated, monovalent mono- or bicyclic hydrocarbon moiety of three to ten ring carbons. The cycloalkyl can be optionally substituted with one or more, preferably one, two, or three, substituents within the ring structure. When two or more substituents are present in a cycloalkyl group, each substituent is independently selected.

"Cycloalkylalkyl" refers to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Heteroaryl" means a monovalent monocyclic, bicyclic, tricyclic, or tetracyclic aromatic moiety of 5 to 20 ring atoms containing one, two, or three ring heteroatoms selected from N, O, or S, the remaining ring atoms being C. The heteroaryl ring is optionally substituted independently with one or more substituents, often one or more substituents, each of which is independently selected from alkyl, haloalkyl, heteroalkyl, heterocyclyl, halo, nitro, cyano, carboxy, acyl, -(alkylene)$_n$—COOR (where n is 0 or 1 and R is hydrogen, alkyl, optionally substituted phenylalkyl, or optionally substituted heteroaralkyl), or -(alkylene)$_n$—$CONR^aR^b$ (where n is 0 or 1, and $R^a$ and $R^b$ are, independently of each other, hydrogen, alkyl, cycloalkyl, cycloalkylalkyl, hydroxyalkyl, aryl, or $R^a$ and $R^b$ together with the nitrogen atom to which they are attached form a heterocyclyl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Heterocyclyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected.

"Protecting group" refers to a moiety, except alkyl groups, that when attached to a reactive group in a molecule masks, reduces or prevents that reactivity. Examples of protecting groups can be found in Greene, T. W. and Wuts, P. G. M., *Protective Groups in Organic Synthesis,* 3rd edition, John Wiley & Sons, New York, 1999, and Harrison and Harrison et al., *Compendium of Synthetic Organic Methods,* Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

Following abbreviations are used for various transition metal ligands:
phen=1,10-phenanthroline
bpy=2,2'-bipyridine
dppz=dipyrido[3,2-a:2',3'-c]phenazine
dmb=4,4'-dimethyl-2,2'-dipyridine
dpdphphz=4,5,9,18-tetraazaphenanthreno[9,10-b]triphenylene
PTZ=phenothiazine Electrochemical Hybridization Detection Some aspects of the present invention will be described with regard to the accompanying drawings which assist in illustrating various features of the invention. In this regard, some aspects of the present invention generally relates to electrochemical detection of an interaction between a substrate and a receptor, e.g., hybridization between an oligonucleotide and a complementary oligonucleotide. That is, some aspects of the invention relate to detecting high affinity selective or specific recognition substrate-receptor interaction, e.g., hybridization, as a sensitive quantitative bio-detection tool using electrochemical analysis. While methods of the invention can be used in detecting a wide variety of substrate-receptor interaction, e.g., oligonucleotide hybridization (RNA, DNA, as well as synthetic olignucleotide derivatives), enzyme-substrate hybridization, for the sake of brevity and clarity, the invention will now be described with regard to detecting hybridization between an oligonucleotide and its complementary oligonucleotide. As stated herein, however, it should be appreciated that the scope of the invention is not limited to detecting hybridization between an oligionucleotide and it's complementary oligionucleotide (or between an oligonucleotide probe and its complementary oligonucleotide target). In this regard, the invention generally relates to detecting selective or specific interaction (e.g., hybridization) between a substrate and a receptor pairing using electrochemistry.

One aspect of the invention provides a method for detecting interaction, e.g., hybridization, between a receptor and a substrate, e.g., an oligonucleotide and its complementary oligonucleotide, based on an electrochemical assay using a probe. The method generally comprises a first transition metal complex and a second transition metal complex. One of the first or the second transition metal complex is a redox transition metal complex that is capable of undergoing a redox reaction. The other of the first or the second transition metal complex is a redox-catalyst complex that is capable of catalyzing the redox reaction of the redox transition metal complex.

One aspect of the invention comprises:
providing an electrode comprising:
a conductive surface, and
a probe that is bound to the conductive surface and is capable of binding to a target substrate;
contacting the conductive-surface bound probe with the test sample to form a surface bound target complex if the target substrate is present in the test sample, wherein the surface bound target complex further comprises a first redox complex;
contacting the surface bound probe or the surface bound target complex, if present, with a fluid medium comprising a second redox complex, wherein one of the first or the second redox complex is a redox transition metal complex that is capable of undergoing an oxidation-reduction reaction and the other of the first or the second redox complex is a redox-catalyst complex that is capable of catalyzing the oxidation-reduction reaction of the redox transition metal complex;
detecting the oxidation-reduction reaction of the redox transition metal complex that is at least in part catalyzed by the redox-catalyst complex; and
determining the presence or absence of the target substrate in the test sample from the detected oxidation-reduction reaction.

Various methods that have been developed for the detection of differences between DNA sequences rely on hybridization events to differentiate native versus mutated sequences and are limited by the small differences in base-pairing energies caused by point mutations within extended polynucleotides. Typically, a nucleic acid hybridization assay to determine the presence of a particular nucleotide sequence (i.e. the "target sequence") in either RNA or DNA comprises a multitude of steps. First, an oligonucleotide probe having a nucleotide sequence complementary to at least a portion of the target sequence is labeled with a readily detectable atom or group. When the labeled probe is exposed to a test sample suspected of containing the target nucleotide sequence, under hybridizing conditions, the target will hybridize with the probe. The presence of the target sequence in the sample can be determined qualitatively or quantitatively in a variety of ways, usually by separating the hybridized and non-hybridized probe, and then determining the amount of labeled probe which is hybridized, either by determining the presence of label in probe hybrids or by determining the quantity of label in the non-hybridized probes. Suitable labels may provide signals detectable by luminescence, radioactivity, colorimetry, x-ray diffraction or absorption, magnetism or enzymatic activity, and may include, for example, fluorophores, chromophores, radioactive isotopes, enzymes, and ligands having selective or specific binding partners. However, the selective or specific labeling method chosen depends on a multitude of factors, such as ease of attachment of the label, its sensitivity and stability over time, rapid and easy detection and quantification, as well as cost and safety issues. Thus, despite the abundance of labeling techniques, the usefulness, versatility and diagnostic value of a particular system for detecting a material of interest is often limited.

Methods of the invention are directed to using electrochemical method of detecting hybridization. In particular, methods of the invention utilize detecting a redox reaction between the redox transition metal complex and the redox-catalyst complex. In some embodiments, the electric potential is applied to the electrode and/or the fluid medium such that the redox reaction of the redox transition metal complex in the surface bound target complex occurs only minimally, if at all, in the absence of the redox-catalyst complex. In this manner, detection of a significant amount of redox reaction corresponds to the presence of surface bound target complex.

As stated herein, methods of the invention are useful in a variety of applications. In one particular embodiment, methods of the invention are particularly useful in the diagnosis of genetic diseases that arise from point mutations. For example, many cancers can be traced to point mutations in kinases, growth factors, receptors binding proteins and/or nuclear proteins. Other diseases that arise from genetic disorders include cystic fibrosis, Bloom's syndrome, thalassemia and sickle cell disease. In addition, several specific genes associated with cancer, such as DCC, NF-1, RB, p53, erbA and the Wilm's tumor gene, as well as various oncogenes, such as abl, erbB, src, sis, ras, fos, myb and myc have already been identified and examined for specific mutations.

Among its many applications, some aspects of the invention provide methods for detecting single or multiple point mutations. It should be appreciated that methods of the invention can be used alone or in combination with other hybridization-dependent methods.

Figure 2:
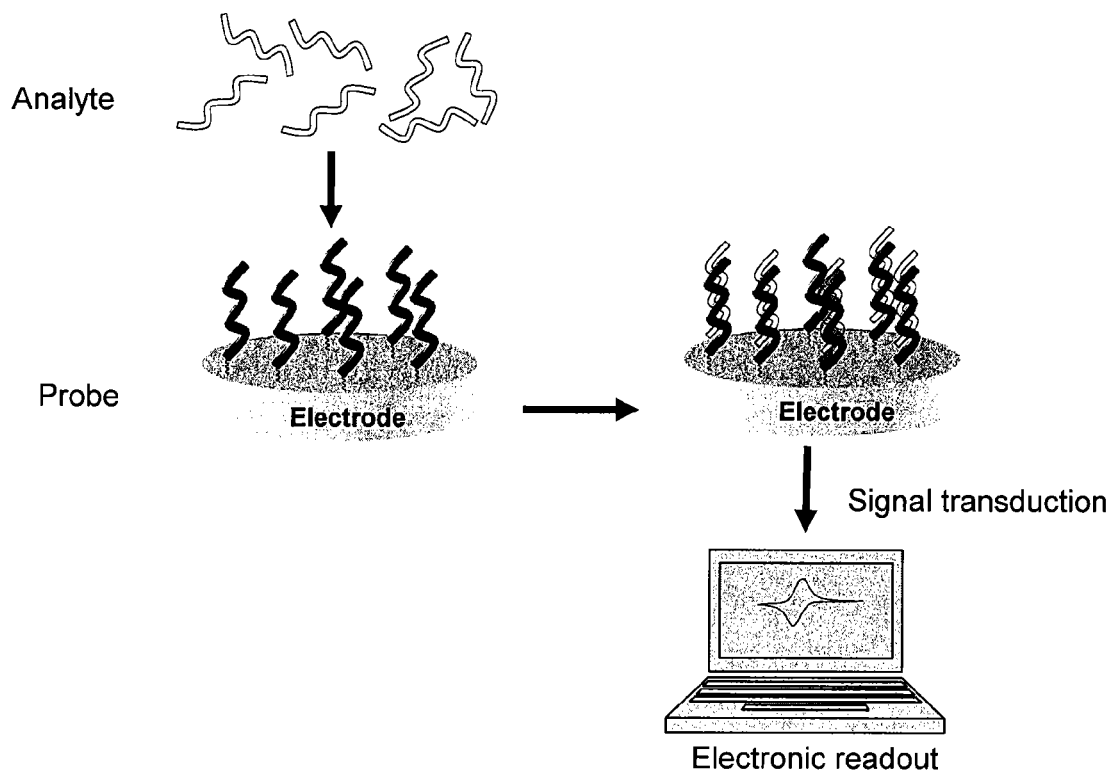
FIG. 2 is a schematic illustration of principles of electrochemical DNA analyte capture detection on electrode surfaces using double-strand hybridization.

One aspect of the invention, e.g., general principles of electrochemical DNA analyte capture detection on electrode surfaces using double-strand hybridization, is schematically illustrated in FIG. 2. As shown in FIG. 2, unknown target DNA sequences in solution (white) are captured, if complementary, by surface-immobilized ssDNA probes (black) on the electrode. Hybridization events are detected by exploiting appropriate redox active indicators selective or specific for the surface-complexed dsDNA (i.e., surface bound target complex). Current proportional to numbers of surface-complexed dsDNA formed and numbers of electroactive mediators (i.e., redox-catalyst complexes) recruited to (i.e., interacting with) the surface-complexed dsDNA can be used for analysis. Enzymatic mediators (i.e., enzymatic redox-catalyst complexes) can exploit multiple redox cycles in the presence of surface bound target complex to enhance signal production and sensitivity.

Some aspects of the invention provide highly sensitive electrochemical detection techniques, and detection of sub-picomolar quantities of hybridized target DNA. Such techniques can include an electrocatalytic step coupled to heterogeneous electron transfer from the dsDNA-associated redox mediator. On certain semiconductor metal oxide electrode materials, including $SnO_2$ and $In_2O_3$ and their combinations (ITO), these hybridized dsDNA complexes (i.e., surface bound target complex) amplify electrical current produced from electrochemical oxidation of redox-active species bound to the surface. In some embodiments, this catalytic process provides a powerful tool in DNA electrosensor detection capabilities. For example, in one study, it has been shown that certain redox active metal complexes can be immobilized on ITO. See, for example, the Examples section below. In one particular instance, in the presence of specific Co(II) polypyridyl complexes, it was observed that the redox-catalyst complex amplified the current >100-fold compared to similar conditions in the absence of the redox-catalyst complex. Without being bound by any theory, the substantial amplification is attributed to an $E_{surface}C'$ mechanism whereby the adsorbed complex catalytically oxidizes the Co complex in solution.

Redox Transition Metal Complex

Redox transition metal complexes are comprised of a transition metal that is capable of undergoing reduction-oxidation reaction. In some embodiments, the redox transition metal is present in the fluid medium.

In other embodiments, the redox transition metal is bound to at least one ligand that comprises a moiety that is either attached covalently or is capable of being bound to the surface bound target complex. For example, when the surface bound target complex is a dsDNA in which the probe oligonucleotide is hybridized to the target substrate, the redox transition metal complex comprises a ligand that can intercalate into the dsDNA. A variety of dsDNA intercalating agents are known to one skill in the art. For examples, Phenothiazine and its N-alkyl derivatives, see, for example, Wang et al., *Analytica Chimica Acta,* 1996, 332, 139-144; Vanickova et al., *Chem. Anal. (Warsaw),* 2000, 45, 125; Yabuki et al., *Bioelectrochemistry,* 2004, 63, 253-255; Zhong et al., *Analytical Sciences,* 2003, 19 (5), 653; Erdem et ct., Electroanalysis, 2002, 14(14), 965; Phenoxazine and its N-alkyl derivatives, see, for example, Chandramouli et al., *Nucleosides, Nucleotides & Nucleic Acids,* 2004, 24(10), 1639; Dipyrido[3,2-a:2',3'-c]phenazine, see, for example, Maheswari et al., *Journal of Inorganic Biochemistry* 2006, 100(1), 3-17; Phillips et al., *Biochemistry* 2004, 43(43), 13657-13665; Zhang et al., *Journal of Inorganic Biochemistry* 2004, 98(8), 1405-1412; Mudasir et al., *Zeitschriftfuer Naturforschung, B: Chemical Sciences* 2004, 59(3), 310-318; Ortmans et al., *Dalton Transactions* 2004, 4, 668-676; 4,5,9,18-tetraazaphenanthreno[9,10-b]triphenylene, see, for example, Zhang et al., *Journal of Inorganic Biochemistry* 2004, 98(8), 1405-1412; Zhen et al., *Journal of Inorganic Biochemistry* 1999, 76(1), 47-53; Zhen et al., *Inorganica Chimica Acta* 2000, 303(2), 141-147; Liu et al., *Journal of the American Chemical Society* 2005, 127(31), 10796-10797; Zhang et al., *Transition Metal Chemistry (Dordrecht, Netherlands)* 2005, 30(3), 285-289; 10-Phenanthroline, see, for example, Williams et al., *Nucleic acids research* 1988, 16(24), 11607-15; Stockert, *Journal of theoretical biology* 1989, 137(1), 107-11; Mital et al., *Journal of inorganic biochemistry* 1990, 40(2), 111-20; Acridine, see, for example, Sun et al., *Proceedings of the National Academy of Sciences of the United States of America* 1989, 86(23), 9198-202; Kuruvilla et al., *Journal of Physical Chemistry B* 2005, 109 (46), 21997-22002; Pritchard et al., *Nature (London, United Kingdom)* 1966, 12(5068), 1360-1, all of which are incorporated herein by reference in their entirety.

In one aspect of the invention, the redox transition metal complex is of the formula:

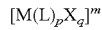   I where
  m is an integer;
  p is an integer from 1 to 6;
  q is an integer from 0 to 5;
  provided that the sum of p+q is such that M has no more than six binding sites;
  M is a transition metal that can exist in at least two stable oxidation sates within the transition metal complex;
  each X is a ligand independently selected from the group consisting of a halide, cyanide, pyridine and amine; and
  each L is independently an optionally substituted aromatic ligand that comprises one, two or three coordinating atoms each of which is independently selected from the group consisting of nitrogen, oxygen, and phosphorous.

In some embodiments, each L is independently selected from the group consisting of bipyridine, terpyridine, and phenanthroline, each of which is optionally substituted.

Still in other embodiments, M is Co.

Yet in other embodiments, at least one of the aromatic ligand of redox transition metal complex I is substituted with a substituent having a steric bulk volume larger than a methyl group. Within these embodiments, in some instances each of the aromatic ligand is independently selected from the group consisting of:

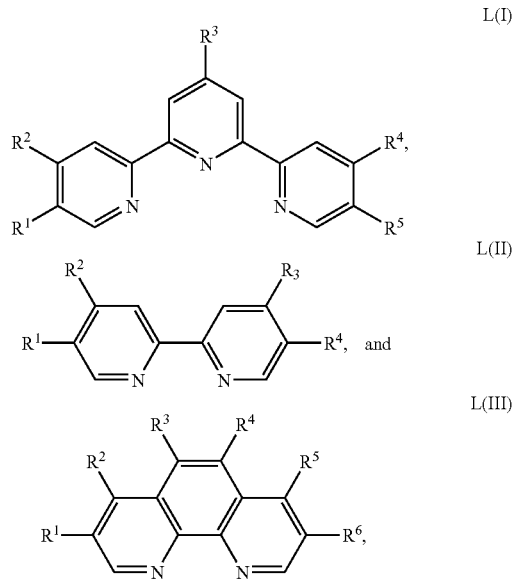

where
  each of $R^1$, $R^2$, $R^3$, $R^4$, $R^5$, and $R^6$ is independently hydrogen, alkyl, cycloalkyl, aryl, aralkyl, an ester moiety of the formula —$CO_2R^7$, an amide moiety of the formula —$CONR^8R^9$;
  $R^7$ is alkyl, cycloalkyl, aryl, or aralkyl; and
  each of $R^8$ and $R^9$ is independently hydrogen, alkyl, cycloalkyl, aryl, or aralkyl;
  provided at least one of $R^1$, $R^2$, $R^4$, or $R^5$ in L(I), or at least one of $R^1$, $R^2$, $R^3$, or $R^4$ in L(II), or at least one of $R^1$, $R^2$, $R^3$, $R^4$, $R^5$, or $R^6$ in L(III) is a substituent having a steric bulk volume larger than a methyl group.

In one particular embodiment, the redox transition metal complex is of the formula: $[M(L(I))_2]^{+m}$, $[M(L(II))_3]^{+m}$, or $[M(L(III))_2]^{+m}$.

Other redox transition metal complexes that are useful in the invention are disclosed in commonly assigned U.S. Pat. No. 7,019,138, which is incorporated herein by reference in its entirety.

The redox transition metal complex and the electrode are selected such that the redox transition metal complex is substantially kinetically inert to redox (i.e., reduction-oxidation) reaction on the electrode surface. For example, when the redox transition metal complex is a cobalt species, electrode is doped $SnO_2$ or ITO.

Methods of the invention include contacting the redox transition metal complex with a surface bound target complex in which a redox-catalyst complex is bound to the surface bound target complex. It should be noted that the redox-catalyst complex is present when the probe and the target substrate forms a surface bound target complex. In the absence of such a surface bound target complex, only an insignificant amount, if any, of redox-catalyst complex is present on the electrode. The redox-catalyst complex is selected such that the redox reaction of the redox transition metal complex is catalyzed by the presence of the redox-catalyst complex.

In some embodiments, the target oligonucleotide is labeled by covalently attaching the redox-catalyst complex to form a labeled target oligonucleotide. Duplexing (i.e., hybridizing) the labeled target oligonucleotide with its surface bound complement (i.e., the probe oligonucleotide) serves to attach the redox-catalyst complex to the electrode surface. The presence of electrode surface bound redox-catalyst complex catalyzes the redox reaction of the redox transition metal complex thereby resulting in current flow in the external circuit. Accordingly, a significant amount of current flow occurs only when the surface bound target complex is present on the electrode surface that can catalyze the redox reaction of redox transition metal complex. Typically, the process is catalytic; therefore, considerable amplification of the current results (i.e., many more electrons are produced than the number of surface bound target complex is present). Such an amplification of signal provides a very high sensitivity for detection of the surface bound target complex.

Redox-Catalyst Complex

Redox-catalyst complexes are comprised of a moiety that is capable of catalyzing the redox reaction of the redox transition metal complex. Typically, the redox-catalyst complex comprises a moiety that is either attached covalently to or is capable of being bound to the surface bound target complex. For example, when the surface bound target complex is a dsDNA in which the probe oligonucleotide is hybridized to the target substrate, the redox-catalyst complex comprises a ligand that can intercalate into the dsDNA or is covalently bound to either the probe oligonucleotide or the target substrate. As discussed above, a variety of dsDNA intercalating agents are known to one skill in the art.

In one aspect of the invention, the redox-catalyst complex is another transition metal complex of the formula:

$$[M^1(L^1)_a(X^1)_b]^n \qquad \text{II}$$

where n is an integer;

a is an integer from 1 to 6;

b is an integer from 0 to 5;

provided that the sum of a+b is such that $M^1$ has no more than six binding sites;

$M^1$ is a transition metal that can exist in at least two stable oxidation sates within the transition metal complex;

each $X^1$ is a ligand independently selected from the group consisting of a halide, cyanide, pyridine and amine; and each $L^1$ is independently an optionally substituted aromatic ligand that comprises one, two or three coordinating atoms each of which is independently selected from the group consisting of nitrogen, oxygen, and phosphorous, and wherein at least one of the aromatic ligand comprises a linker that is attached to a binding moiety that is capable of binding to a double stranded oligonucleotide.

In some embodiments, $M^1$ of redox-catalyst complex of Formula II is Ru, Fe, or Os.

Still in other embodiments, ligands that comprise an intercalating agent is of the formula:

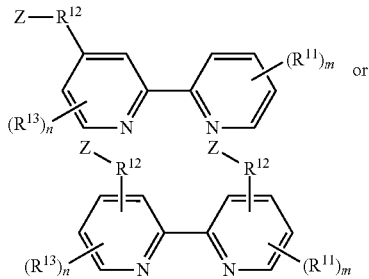

wherein
each m is independently an integer from 0 to 4;
each n is independently an integer from 0 to 3;
each $R^{11}$ is independently alkyl, or aryl, in some embodiments, each $R^{11}$ is independently alkyl;
each $R^{12}$ is independently $C_1$-$C_{12}$ alkylene;
each $R^{13}$ is independently alkyl or aryl, in some embodiments, each $R^{13}$ is independently alkyl; and
each Z is an intercalating moiety that is capable of intercalating into a double stranded oligonucleotide.

Within these embodiments, in some instances m is 1. Still in other instances, $R^{11}$ is methyl. Yet in other instances, n is 0.

Typically, each aromatic ligand, $L^1$, is independently an optionally substituted monocyclic, bicyclic, tricyclic, or tetracyclic heteroaryl moiety having one, two, three, or four ring heteroatoms each of which is independently selected from N, O, and S. In many instances, each aromatic ligand is independently an optionally substituted bicyclic or tricyclic heteroaryl moiety having two or three ring heteroatoms. Typically, the ring heteroatom is nitrogen. In one particular embodiment, each $L^1$ is independently selected from the group consisting of dppz, dpphz, dmb, bpy, phen, and dpdphphz.

Figure 3:
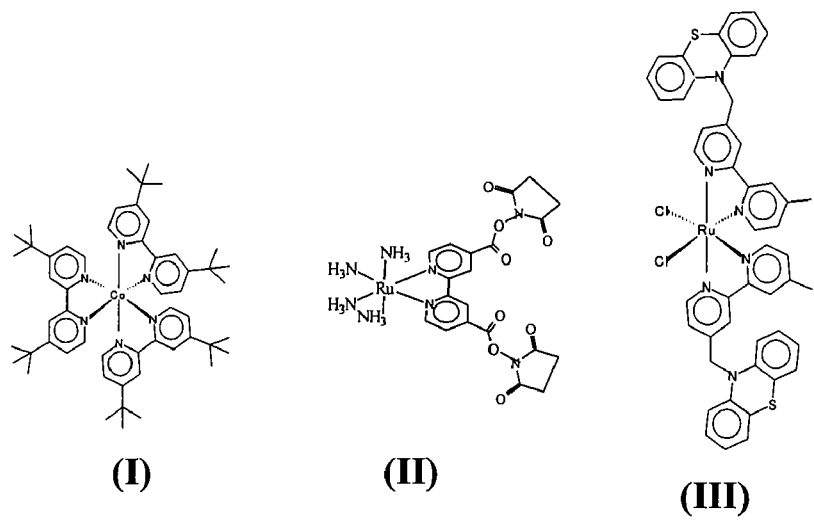
FIG. 3 shows a representative cobalt complex (I), and electrochemically active DNA labels: $Ru(NH_3)_4(NHS_2 \, bpy)]Cl_2$ (II) and $[Ru(41\text{-}PTZ\text{-}bpy)_2Cl_2]$ (III).

In some embodiments, the redox-catalyst complex is selected from the group consisting of Ru(dppz)$_2$Cl$_2$, Ru(dmb)(dpphz)Cl$_2$, Os(dppz)$_2$Cl$_2$, Os(bpy)(dpphz)Cl$_2$, Os(dpphz)(phen)Cl$_2$, Os(dpdphphz)(phen)Cl$_2$, [Os(phen)(dppz)(py)Cl]PF$_6$, and [Os(bpy)(dpdphphz)(py)Cl]PF$_6$. These redox-catalyst complexes are particularly useful in detecting hybridization of an oligonucleotide probe with its substantially complementary target oligonucleotide. In particular, these redox-catalyst complexes comprise an intercalating moiety that can bind to a double stranded oligonucleotide. In this manner, the redox-catalyst complex binds to a double stranded oligonucleotide, e.g., when the surface bound target complex between a probe oligonucleotide and the target oligonucleotide is present, and no significant amount, if any, of binding occurs with a single stranded oligonucleotide. It should be appreciated that often intercalation of intercalating moiety to a double stranded oligonucleotide is a non-covalent linkage. Accordingly, in these embodiments, the redox-catalyst complex is typically added after the surface bound target complex has formed (e.g., double stranded oligonucleotide formation between a probe oligonucleotide and a substantially complementary target oligonucleotide). See, for example, FIG. 3, compound III, which is an illustrative example of a redox-catalyst complex that can be used to intercalate into a double stranded oligonucleotide after the double stranded oligonucleotide has formed between a probe oligonucleotide and a substantially complementary target oligonucleotide. In compound III of FIG. 3, phenothiazine (PTZ) moiety is the intercalating moiety that binds to a double stranded oligonucleotide.

Alternatively, the redox-catalyst complex can be covalently linked to a target oligonucleotide. The term "probe" is used to designate the compound or moiety that is bound to the surface of the electrode, whereas the "target substrate" refers to a corresponding substantially complementary compound or moiety that forms a duplex or a surface bound target complex. Accordingly, in some aspects of the invention, after the probe is bound to the surface of the electrode, it is contacted (or exposed) to a sample which may or may not comprise the target substrate. Regardless of whether the target substrate is present in the sample, the sample is treated with an appropriate reagent to covalently link the redox-catalyst complex to the target substrate. For example, oligonucleotides can be labeled with a redox-catalyst complex such as compound II of FIG. 3. In particular, the N-hydroxy succinimide moiety of compound II of FIG. 3 can be used to covalently link the redox-catalyst complex II to a target oligonucleotide to produce a labeled target oligonucleotide. When the labeled target oligonucleotide is contacted with (or exposed to) the probe that is substantially complementary to the target oligonucleotide and is bound to the surface of the electrode, it forms a double stranded oligonucleotide via hybridization. The electrode is then washed to remove any unbound target substrate. The resulting electrode then comprises any remaining surface bound probe molecules and surface bound target complex provided that the test sample comprises an oligonucleotide that is substantially complementary to the probe oligonucleotide. In this manner, substantially only the redox-catalyst complex that is bound to the target oligonucleotide that hybridized with the probe remains on the surface of the electrode.

By measuring the electrochemical reaction of the redox transition metal complex that is catalyzed by the redox-catalyst complex present on the surface bound target complex, one can determine the presence and/or the quantity of the surface bound target complex.

Accordingly, methods of the invention include contacting the electrode with a fluid medium comprising a redox transition metal complex. The redox transition metal complex undergoes redox reaction in the presence of the redox-catalyst complex. When the redox-catalyst complex is absent, only a minute amount, if any, of redox reaction occurs from the redox transition metal complex.

In other embodiments, the redox-catalyst complex does not comprise any metal (e.g., a transition metal) coordination complex. In these embodiments, the redox-catalyst complex is often organic compound or in some instances is organometallic compounds, i.e., contains metal-carbon bonds (collectively "organic redox-catalyst"). Typically, the organic redox-catalyst complex comprises an aromatic moiety that can catalyze a redox reaction of the redox transition metal complex and a binding moiety that can bind to the surface bound target complex. Such binding moiety are discussed above. Exemplary organic redox-catalyst complexes include the following compounds; however, it should be appreciated that organic redox-catalyst complexes are not limited to those shown below. In fact, any organic redox-catalyst complex that can (1) catalyze the redox reaction of the transition metal complex disclosed herein; and (2) have a binding moiety that can bind (either covalently or non-covalently) to the surface bound target complex, are within the scope of the present invention.

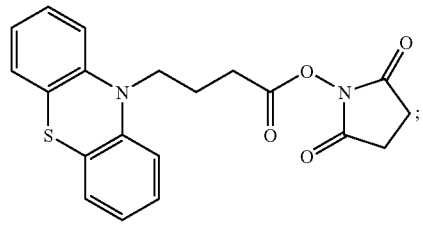

1

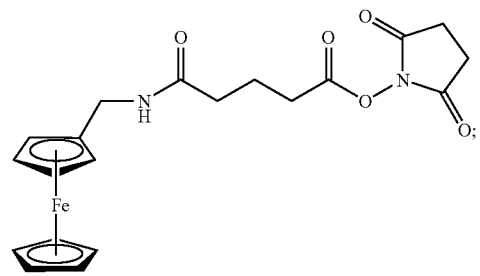

2

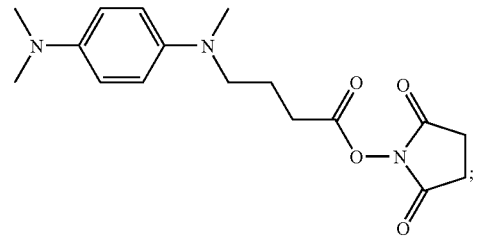

3

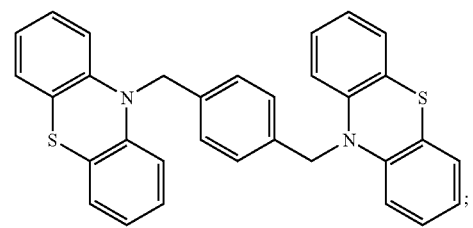

1'

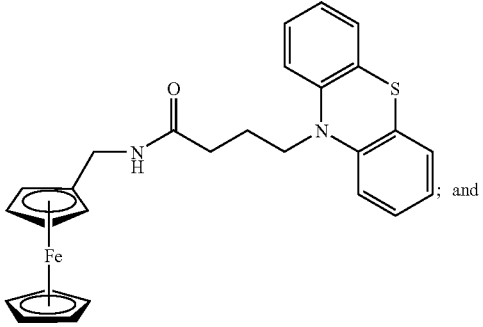

2'

; and

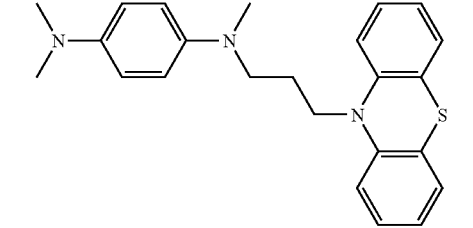

3'

Compounds 1, 2, and 3 can be covalently attached to the target DNA through the amide bond; and the phenylthiazine moiety of Compounds 1', 2' and 3' can be intercalate into dsDNA.

Electrode

As stated above, the electrode material is selected such that the redox reaction of the redox transition metal complex does not occur in any appreciable amount in the absence of the redox-catalyst complex. For example, for the redox transition metal complexes that are disclosed in a commonly assigned U.S. Pat. No. 7,019,138, the electrode material is typically made of, but is not limited to, $SnO_2$ and $In_2O_3$ and combinations thereof (ITO). The electrode can also be a microarray, consisting of a number of separately addressable electrodes, or an ultramicroelectrode.

To avoid oxidation of the DNA bases, the redox potential of redox transition metal complex is typically about 800 mV or less, often 600 mV or less, and more often 400 mV or less, relative to SCE. Typically, in the case where the redox transition metal complex undergoes oxidation in the process of sensing the target-probe complex on the electrode surface, generally no significant amount of oxidation current flows at potentials negative of about 800 mV (vs. SCE) in the absence of the redox-catalyst complex. Without being bound by any theory, the absence of significant current is attributed to slow heterogeneous electron transfer between the electrode and the redox transition metal complex. In this manner, the redox transition metal complex does not undergo any significant amount of oxidation when a potential of less than about 800 mV is applied to the electrode. When the redox-catalyst complex is present, it catalyzes the redox reaction of the redox transition metal complex. Thus, the presence of redox reaction (e.g., observation of a significant amount of current flow) indicates the presence of surface bound target complex, e.g., duplexed oligonucleotide.

Typically, in the case where the redox transition metal complex undergoes reduction in the process of sensing the target-probe complex on the electrode surface, no significant amount of reduction current flows at potentials positive of about −500 mV (vs. SCE) in the absence of the redox-catalyst complex. Without being bound by any theory, the absence of significant current is attributed to slow heterogeneous electron transfer between the electrode and the redox transition metal complex. In this manner, the redox transition metal complex does not undergo any significant amount of reduction when a potential of less than the about −500 mV is applied to the electrode. When the redox-catalyst complex is present, it catalyzes the redox reaction of the redox transition metal complex. Thus, the presence of redox reaction (e.g., observation of a significant amount of current flow) indicates the presence of surface bound target complex, e.g., duplexed oligonucleotide.

Oligonucleotide Detection

Some aspects of the invention utilize redox reaction catalysis for nucleic acid hybridization detection. ITO electrodes are first modified with ssDNA which is then duplexed with its complement. This dsDNA is redox labeled (either pre- (FIG. 3, complex II) or post-duplexing (FIG. 3, complex III), vide infra) and the electrochemical oxidation of the label is amplified by the catalytic oxidation of the Co(II) complex (FIG. 3, complex I) in solution. In some embodiments, this catalytic electrochemical method provides detection of hybridized dsDNA surface concentrations on the order of picomoles/$cm^2$.

Additional objects, advantages, and novel features of this invention will become apparent to those skilled in the art upon examination of the following examples thereof, which are not intended to be limiting.

EXAMPLES

Materials

Photoresist AZ1512 was obtained from Clariant Corporation. ACS-grade solvents and reagents from Fisher were used for synthesis, electrode preparation and functionalization. Optima-grade acetonitrile (Fisher) was used for electrochemical studies. Tetra-n-butylammonium hexafluorophosphate ($TBAPF_6$), 2,2,6,6-tetramethylpiperidinooxy (TEMPO) (99%), 4,4'di-tert-butyl-2,2'-bipyridine (DTB), iron(II) perchlorate hydrate, N-hydroxysuccinimide (NHS), phenothiazine (PTZ) and hydrated hydrazine (98%) were purchased from Aldrich Chemicals. 1-(3-dimethylamino) propyl)-3-ethylcarbodiimide hydrochloride (EDC), tris hydroxymethyl aminomethane hydrochloride (Tris), disodium ethylenediamine tetraacetate (EDTA), sodium dodecyl sulfate (SDS) and sodium citrate were purchased from Fisher Scientific. $RuCl_3$ was obtained from Johnson Matthey. 4,4-Dimethyl-2,2'-bipyridine (DMB) (obtained from Reilley Industries) was recrystallized from ethyl acetate. Cobalt(II) perchlorate hydrate was obtained from GFS Chemical Company. 2,2'-Bipyridine-4-4'-dicarboxylic acid (DCB) was prepared according to a literature procedure. See, Nazeeruddin, et al., *Inorganic Syntheses*, 1998, 32, 181. Unless otherwise noted, all reagents were used without further purification. Low resistance (4-8Ω) ITO glass slides were purchased from Delta Technologies Ltd (Stillwater, Minn.). DNA oligonucleotides were purchased from MWG Biotech Inc. (High Point, N.C.). The chosen oligonucleotide sequence, 5'-CTGAACG-GTAGCATCTTGAC, (ssDNA probe) forms a stable duplex with its complementary pair at room temperature, with minimal interference due to self-complementarity or secondary structure.

Redox-Active Reagent Preparations

[Co(DTB)$_3$](ClO$_4$)$_2$, (I) (Sapp et al., *J. Am. Chem. Soc.*, 2002, 124 (37), 11215-11222), [Ru(NH$_3$)$_5$Cl]Cl$_2$ (IV) (Allen et al., Inorganic Syntheses 1970, 12, 2-8), and [Ru(NH$_3$)$_5$ H$_2$O]PF$_6$ (V) (Sheridan et al., Inorganic Chemistry, 1972, 11(11), 2721) were prepared as reported previously. The ligand 4-(N-phenothiazinylmethyl), 4'-methyl-2,2'-bipyridine (41-PTZ-bpy) was prepared from 4-bromomethyl,4'-methyl-2,2'-bipiridine via a literature procedure (Larson et al., J. Phys. Chem. 1995, 99, 6530-6539), as was the ruthenium complex, [Ru(41-PTZ-bpy)$_2$Cl$_2$], (III).

In order to characterize complex I by NMR spectroscopy, the paramagnetic Co(DTB)$_3$$^{2+}$ was oxidized to diamagnetic Co(DTB)$_3$$^{3+}$ by adding a slight excess of the oxidant NOBF$_4$ to an acetonitrile solution of the reduced form. Oxidation was complete almost instantaneously. The mixed salt, [Co (DTB)$_3$](ClO$_4$)$_x$(BF$_4$)$_{3-x}$, was collected after complete evaporation of the solvent at 50° C. under reduced pressure. During this procedure, the slight excess of NOBF$_4$ present readily decomposes to gaseous products by reaction with trace water in the solvent. The $^1$H NMR is consistent with the D$_3$ geometry of the complex in which all bipyridine ligands are magnetically equivalent ($^1$H NMR, 300 MHz, CD$_3$OD: 9.0 ppm d, 6H, 7.85 ppm m, 6H, 7.3 ppm d, 6H, 1.5 ppm s, 54H).

2,2'-Bipyridine-4,4'-dicarboxylic acid bis N-succinimidyl ester (NHS$_2$bpy)

2,2' Bipyridine-4,4'-dicarboxylic acid (1.0 g, 4.098×10$^{-3}$ mol) and 0.94 g of NHS (8.2×10$^{-3}$ mol) were suspended in 100 ml DMF. DDC (1.68 g, 8.2×10$^{-3}$ mol), dissolved in 20 ml DMF, was then slowly added to the reaction mixture with an addition funnel. The reaction was stirred at room temperature for 16 hours. Periodic monitoring of the formation of the desired NHS ester was done by TLC on silica gel using a mixture of MeOH/AcOEt 1:9 (R$_f$ of product=0.9, R$_f$ for dicarboxylic acid=0). Partially insoluble urea, formed during the condensation, was removed by suction filtration and the clear filtrate was evaporated to dryness. Dichloromethane was added to the solid residue under gentle heating. The ester product dissolved while the dicyclohexylurea by-product did not and was removed by filtration. The resulting clear solution was concentrated under reduced pressure until precipitation of the ester began. The resulting mixture was then cooled at −20° C. The NHS ester was then collected on a glass frit, washed with cold dichloromethane and dried under vacuum. $^1$H NMR 300 MHz (CDCl$_3$) (9.2 ppm s 2H, 9 ppm d 2H, 8.1 dd 2H, 3 s 8H). Elemental analysis: Calculated: N 12.78%, C 54.79%, H 3.19%. Found: N 12.93%, C 54.43%, H 3.61%.

[Ru(NH$_3$)$_5$(NHS$_2$bpy)](PF$_6$)$_2$                       (II)

[Ru(NH$_3$)$_5$OH$_2$](PF$_6$)$_2$, freshly prepared from 0.145 g of [Ru(NH$_3$)$_5$Cl]Cl$_2$, was immediately used for the reaction with freshly prepared NHS ester. [Ru(NH$_3$)$_5$OH$_2$](PF$_6$)$_2$ was dissolved in 10 ml DMF previously degassed with argon. The color of the solution turned immediately green ostensibly due to formation of the solvent complex [Ru(NH$_3$)$_5$DMF](PF$_6$)$_2$. NHS$_2$ bpy (0.181 g dissolved in 5 ml of degassed DMF) was then added and the solution turned from green to red-brown. The reaction continued for 8 hours at room temperature under argon atmosphere, was then filtered and the product precipitated by addition of excess diethyl ether. The red-brown solid was collected on a sintered glass crucible, washed with ether and dried at room temperature. The reaction product, [Ru(NH$_3$)$_4$(NHS)$_2$ bpy](PF$_6$)$_2$, was purified by size exclusion chromatography using Sephadex LH 20/methanol.

The water soluble [Ru(NH$_3$)$_4$(NHS)$_2$ bpy]Cl$_2$ salt, II, was obtained by addition of an excess of TBACl to a solution of [Ru(NH$_3$)$_4$(NHS)$_2$ bpy](PF$_6$)$_2$ in acetone. The precipitate was collected by suction filtration, washed with ether and dried under vacuum. $^1$H NMR 300 MHz (CD$_3$CN): (9.2 d 2H, 8.8 s 2H, 7.8 m 2H). These signals are believed to originate from aromatic protons of the bipyridine moiety. Broad signals at 7.4 and 6.4 ppm are believed to be due to axial and equatorial ammonium protons that exchange with the solvent. The NHS group gives rise to two characteristic resonances at 3.3 and 2.9 ppm that integrate to 4 protons each, as expected, given the symmetry of the ligand and the complex. UV-V is: 550 and 416 nm MLCT bands, 312, 240 and 209 nm LC transitions.

10-Methylphenoxazine (Me-POZ), 10-Methylphenothiazine (Me-PTZ), and 10-methylphenoselenazine (Me-PSZ)

The synthesis and characterization of Me-POZ (Zhu et al., Chemistry of Materials 2005, 17(21), 5225-5227) and Me-PSZ (Muller et al., Journal of Organic Chemistry 1959, 24, 37-9) have been reported previously. Me-PTZ was obtained from Aldrich and recrystallized three times from 10:1 toluene-hexanes yielding a colorless crystalline solid.

10-(4-(4'-methyl-2,2'-bipyridin-4-yl)butyl)-10H-phenoxazine (44-POZ)

A procedure from the literature (Larson et al., J. Phys. Chem. 1995, 99, 6530-6539) was modified as follows: in a drybox under N$_2$ atmosphere, phenoxazine (0.45 g, 2.46 mmol) was combined with NaH (0.0531 g, 1.48 mmol), a catalytic amount of NaI, and 4-(4-bromobutyl)-4'-methyl-2,2'-bipyidine (0.5002 g, 1.64 mmol) in THF (freshly distilled from Na/benzophenone). The solution was then refluxed for 12 h, quenched with ethanol, then dried by rotary evaporation. Upon silica gel chromatography (20:1 methylene chloride-acetone), 44-POZ (a colorless oil) was isolated. The compound was characterized with NMR, TLC and electrospray mass spectroscopy (M+H 408.3).

10-(4-(4'-methyl-2,2'-bipyridin-4-yl)butyl)-10H-phenoselenazine (44-PSZ)

The compound was prepared, isolated, and characterized by a method analogous to that of 44-POZ given above: phenoselenazine (Muller et al., Journal of Organic Chemistry 1959, 24, 37-9) (0.2446 g, 9.93 mmol); NaH (0.0215 g, 8.96 mmol); 4-(4-bromobutyl)-4'-methyl-2,2'-bipyidine (0.202 g, 6.62 mmol); mass spectroscopy (M+H+H 472.2).

(423-DQ)$^{2+}$(PF$_6$)$_2$

A procedure from the literature (see Bolton et al., Adv. Chem. Ser., 1989, 228, 211 and Elliott et al., J. Amer. Chem. Soc., 1985, 107, 4647) was modified as follows: 1,2-Bis[4-(4-methyl-2,2'-bipyridyl)]ethane (0.70 g, 1.91 mmol) was dissolved in n-heptane with a large excess of diiodopropane (purified over alumina) and the solution was refluxed for 6 days. The crude product, (423-DQ)(I)$_2$, was isolated as a red solid, dissolved in water, and precipitated as the PF$_6^-$ salt. Pure (423-DQ)(PF$_6$)$_2$ was isolated as a purple oil from this solid using soxhlet extraction with methanol. The product was characterized using TLC (eluent 40% H$_2$O-10% KNO$_3$ (aq satd)-50% acetonitrile (4:1:5(vol)) and electrospray mass spectroscopy (M+H 699.4).

Ru(44-POZ)Cl$_2$

A procedure from literature (Larson et al., J. Phys. Chem. 1995, 99, 6530-6539) was modified as follows: in a drybox under N$_2$ atmosphere, Ru(DMSO)$_4$Cl$_2$ (0.1947 g, 0.402 mmol) and LiCl (0.170 g, 4.01 mmol) were dissolved in DMF (dried over molecular sieves) and refluxed until an orange color appeared (30 min.); 44-POZ (0.327 g, 0.803 mmol) dissolved in minimum DMF was added over several minutes and the solution was refluxed for 90 min. After removing from the drybox, upon doubling the volume with H$_2$O, a purple solid precipitated which, upon silica gel chromatography (10:1 methylene chloride-methanol saturated with ammonia), yielded Ru(44-POZ)Cl$_2$ as a purple oil. Light was rigorously excluded throughout the above procedure.

Ru(44-POZ)$_2$(423-DQ)(PF$_6$)$_4$

A procedure from literature (Larson et al., J. Phys. Chem. 1995, 99, 6530-6539) was modified as follows: in a drybox under N$_2$ atmosphere Ru(44-POZ)$_2$Cl$_2$ (0.061 g, 0.062 mmol) was heated to 120° C. in ethylene glycol for 30 min; (423-DQ)(PF$_6$)$_2$ (0.0561 g, 0.080 mmol), dissolved in acetone, was added and the solution was heated for 30 min at 120° C. The mixture was removed from the drybox, diluted with H₂O, and separated as $PF_6^-$ salt using centrifugation; silica gel chromatography (eluent 40% H₂O-10% KNO₃ (aq satd)-50% acetonitrile (4:1:5(vol)) yielded the product as a dark solid. Light was rigorously excluded throughout the above procedure. A combination of TLC, electrospray mass spectroscopy (M+1 1759), and electrochemistry was used for determination of sample integrity.

Ru(44-PSZ)₂Cl₂

The compound was prepared, isolated, and characterized by a method analogous to that of Ru(44-POZ)Cl given above: Ru(DMSO)₄Cl$_n$ (0.0824 g, 0.170 mmol); LiCl (0.150 g, 3.54 mmol); 44-PSZ (0.1683 g, 0.3579 mmol).

Ru(44-PSZ)₂(423-DQ)(PF₆)₄

The compound was prepared, isolated, and characterized by a method analogous to that of Ru(44-POZ)₂(423-DQ)(PF₆)₄ given above: Ru(44-PSZ)₂Cl₂ (0.0796 g, 0.0715 mmol); (423-DQ)(PF₆)₂ (0.06497 g, 0.093 mmol); electrospray mass spectroscopy (M+11885).

Ru(44-PTZ)₂(423-DQ)(PF₆)₄

The preparation of this compound was reported previously (Larson et al., J. Phys. Chem. 1995, 99, 6530-6539).

Preparation of Compounds 1, 2, 3, 1', 2' and 3'

α,α'-Dibromo-p-xylene, N-hydroxysuccinimide (NHS), ethyl 4-bromobutyrate, N,N'-Dicyclohexylcarbodiimide (DCC), and phenothiazine (PTZ) are commercially available from Aldrich.

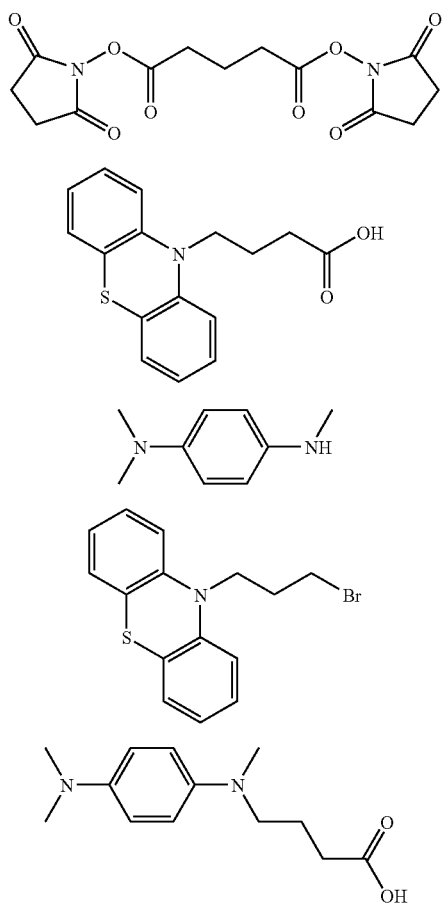

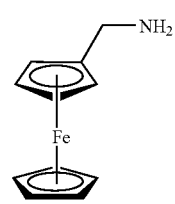

A is prepared from literature procedure. See, for example, Andreev, et al., *Bioorganicheskaya Khimiya*, 1987, 13(5), 696.

B is prepared from literature procedure. See, for example, Huang, et al., *Langmuir*, 1999, 15, 6510).

C is prepared from literature procedure. See, for example, Sekiya, et al., *Chemical and Pharmaceutical Bulletin*, 1967, 15(9), 1339.

D is prepared from literature procedure. See, for example, Kawanishi, et al., *Phys. Chem.* 1986, 90, 2469-2415; and Thomas, et al., *ChemPhysChem*, 2003, http://www3.interscience.wiley.com/cgi-bin/jissue/106570146/4 (12), 1299-1307.

E is prepared by heating C with ethyl 4-bromobutyrate in acetonitrile, the produced ester is refluxed in aqueous sodium carbonate solution to provide the acid E.

F is prepared according to the literature. See, for example, Kraatz, et al., *Journal of Organometallic Chemistry* 1999, 579, 222-226.

Preparation of Compounds 1 and 3

To prepare Compounds 1 and 3, one equivalent amount of NHS is combined with the corresponding starting materials B or E in DMF. One equivalent DCC in DMF is then slowly added to the reaction mixture with an addition funnel. The reaction is stirred at room temperature for 16 hours. Periodic monitoring of the formation of the desired NHS ester is done by TLC on silica gel. Partially insoluble urea, formed during the condensation, is removed by suction filtration and the clear filtrate was evaporated to dryness. Dichloromethane is added to the solid residue under gentle heating. The ester product dissolves while the dicyclohexylurea by-product does not and is removed by filtration. The resulting clear solution is concentrated under reduced pressure to isolate the ester.

Preparation of Compound 2

To prepare Compound 2, F is mixed with excess A in acetonitrile. The solution is refluxed under nitrogen for sometime. TLC is used to monitor the reaction. The product is extracted with water and methylene chloride and purified with a silica column.

Preparation of Compound 1'

Two equivalents of PTZ is dissolved in dry THF and two equivalents of NaH is added under nitrogen at 0° C. The solution is stirred at room temperature for 3 hours. Then the solution of one equivalent of α,α'-dibromo-p-xylene in dry THF is added slowly by cannula. The solution is stirred for a certain amount of time till TLC shows the reaction is complete. The product is extracted with methylene chloride and water, and is purified by a silica column.

Preparation of Compound 2'

Equivalent amounts of Compound 1 and F are dissolved in acetonitrile. The solution is refluxed under nitrogen. TLC is used to monitor the reaction. The product is extracted with methylene chloride and water, and is purified by chromatography using a silica column.

Preparation of 3'

Equivalent amounts of C and D are dissolved in acetonitrile. The solution is refluxed under nitrogen. TLC is used to monitor the reaction. The product is extracted with methylene chloride and water, and purified by chromatography using a silica column.

Preparation of Samples for Kinetic Studies

Samples for kinetic studies were initially prepared in cells as described previously using multiple freeze-pump-thaw cycles (FPT) to remove dissolved oxygen (Larson et al., J. Phys. Chem. 1995, 99, 6530-6539). Samples consisted of a $2.5 \times 10^{-5}$ M solution of the complex in 1,2 dichloroethane (Acros). It was found that a further deoxygenation step was necessary to obtain reproducible kinetics with moderate applied magnetic fields (>300 mT). Once FPT degassed, the samples were taken into a nitrogen filled drybox (below 1 ppm oxygen) and allowed to equilibrate with the box atmosphere (30 min).

Measurements

Cyclic Voltammetry (CV)

A conventional 3-electrode electrochemical cell with a BAS 100B electrochemical analyzer was used for all CV measurements. 0.1 M Tetra-n-butylammonium hexafluorophosphate ($TBAPF_6$) in acetonitrile was used as the electrolyte. A glassy carbon working electrode was used along with a platinum wire auxiliary electrode, and a saturated sodium calomel (SSCE) reference electrode. A scan rate of 200 mV/s was used for all measurements. All solutions were purged with argon prior to electrochemical experiments.

Spectroelectrochemistry

The optically transparent thin layer electrochemical cell (OTTLE) was adapted from the literature (Murray et al., *Anal Chem.*, 1967, 39, 1666). The electrochemical cell consisted of an optically transparent gold minigrid working electrode ($4.33 \times 10^{-2}$ cm path length), a platinum wire auxiliary electrode, and a silver wire quasi-reference electrode. The electrolyte solution consisted of a 1 M tetraethylammonium perchlorate ($TEACIO_4$) solution in acetonitrile. Samples with concentrations of $10^{-3}$ M of the free donor (Me-POZ, Me-PTZ, or Me-PSZ) in electrolyte solution were injected into the optically transparent portion of the cell and a potential 100 mV positive of the first oxidation wave for the donor was applied. The cell was placed perpendicularly to the optical train of a Hewlett Packard 8452A UV-visible spectrometer and electronic spectra were taken at is intervals until the current passing through the cell dropped to a minimal level (usually around 60 s). Extinction coefficient spectra were calculated for the oxidized donors from the resulting data.

Nanosecond Laser Flash Photolysis

A typical magnetic field-dependent transient spectrum was obtained as follows: The frequency-tripled beam of a Quanta-Ray Nd:YAG laser pumped a Spectra Physics PDL-3 dye laser. Coumarin 450 laser dye was used with methanol which was operated at 450 nm. Dye laser power output was typically 85 mW at 30 Hz with a 5-7 ns pulse width. The probe beam was provided by a homebuilt pulser powering a Xenon arc lamp (1 ms pulses). This probe beam was passed through the sample cell, and then focused onto the slit of a Jarrell Ash model 82-310 monochromator. A Hamamatsu R2496 photomultiplier tube measured the intensity of the probe beam and a Tektronix oscilloscope triggered by a Thorlabs DET210 photodiode was used to record and display the data. The experiment was run at 30 Hz and transient signals were averaged over 500 pulses. Magnetic field effect measurements were collected by the placement of the sample between the poles of a Walker Scientific Inc. HV4H electromagnet (Hewlett Packard 6574A power supply) and routing the optical train through the sample. The magnetic field was applied perpendicular to the optical path. Magnetic induction was measured with a Hall probe (F. W. Bell, model 5080).

Electrode Fabrication

ITO electrodes were patterned and cleaned prior to use as described previously (Elliott et al., *Langmuir* 2005, 21, 3022-3027).

Probe DNA Immobilization Procedures

Figure 5:
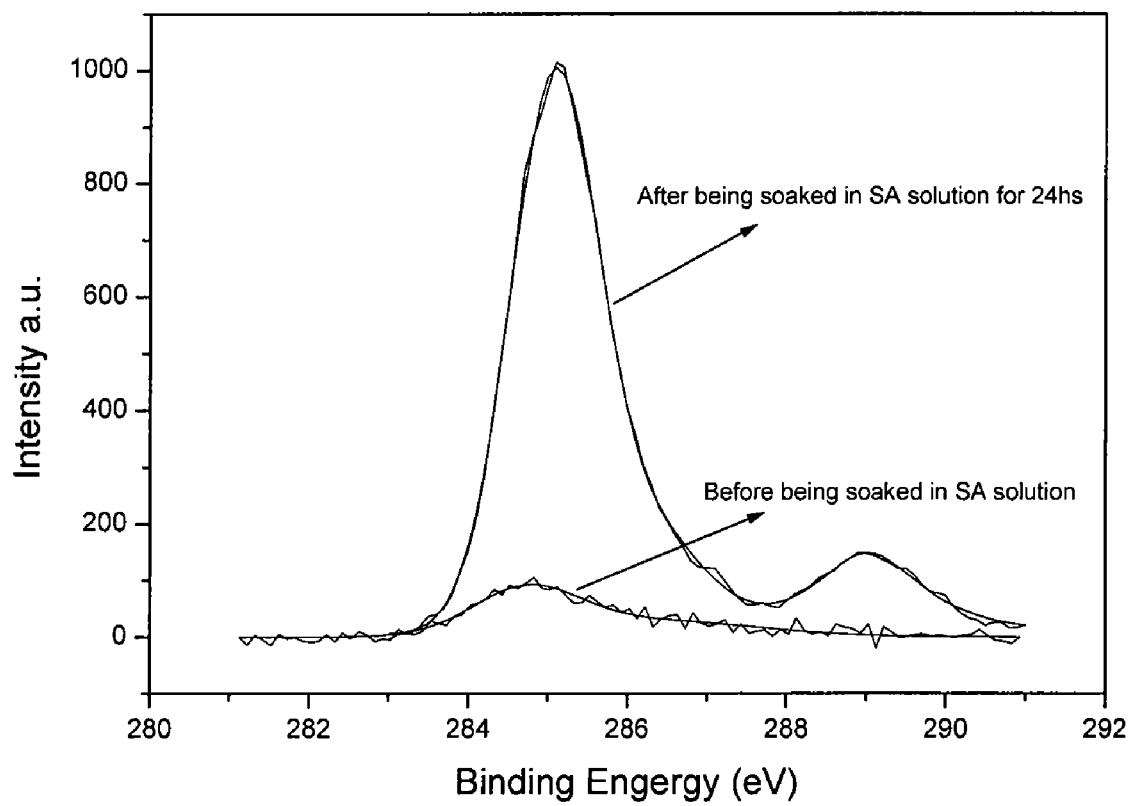
FIG. 5 is a XPS C1s high resolution spectrum (sample depth 2 nm, 15° takeoff angle) of clean ITO sebacic acid-derivatized ITO electrodes.

Clean ITO substrates were immersed in a 0.01M sebacic acid solution in acetonitrile. In 24 hours, the adsorption and the formation of a sebacic acid monolayer was formed as shown from XPS C1s signal comparison before and after treatment with sebacic acid solutions (FIG. 5). The electrodes were then rinsed with acetonitrile and ethanol, dried under nitrogen and analyzed by XPS before oligomeric DNA probe immobilization. 5'-Amine-functionalized oligonucleotide (5' $H_2N$—($CH_2$)-6-GTCAAGATGCTACCGTTCAG) in Millipore-purified water was prepared at 20 micromolar concentration in presence of 1.2 M EDC and 0.24M NHS. A 20-microliter drop of the DNA solution was applied to the sebacic acid-modified ITO electrode and allowed to incubate for 4 hours at room temperature under 75% humidity. The resulting electrodes were briefly rinsed with $H_2O$, followed by a 30-min. immersion in 1M Tris-EDTA saline (TE-NaCl, pH 7.0) to remove residual physisorbed DNA, thoroughly rinsed with water and dried with $N_2$.

Surface density of immobilized DNA was evaluated by radiometric experiments using $^{32}P$-labeled oligonucleotide. DNA oligonucleotide was labeled with radioactive $\alpha$-$^{32}P$-dideoxyadenosinetriphosphate ($\alpha$-$^{32}P$-ddATP, Amersham Biosciences, Piscataway, N.J.) in presence of terminal transferase (Roche Diagnostics Corp., Indianapolis, Ind.) and purified with an oligo mini-spin gel filtration column (Roche Diagnostics Corp., Indianapolis, Ind.). Labeling efficiency of $^{32}P$-labeled oligonucleotides was measured with Tri-Carb5000 liquid scintillation analyzer. $^{32}P$-labeled-oligoDNA stock was then diluted with unlabeled DNA in reaction medium for electrode surface modification steps. The resulting electrode surfaces were exposed to a storage phosphor imager (Amersham Biosciences, Piscataway, N.J.) for radiometric phospho-imaging side by side with $\alpha$-$^{32}P$-ddATP standards spotted onto filter paper. Surface density values were quantified using ImageQuant (Amersham Biosciences, Piscataway, N.J.) software.

DNA Target Hybridization on Probe-Immobilized ITO Surfaces

Hybridization of surface-immobilized DNA probe with its complementary target sequence (5'-$H_2N$—($CH_2$)$_6$—CTGAACGGTAGCATCTTGAC) was performed in 4×SSC/ 0.1% SDS (pH7.0) overnight at 37° C., 100% humidity, with target concentrations ranging from 10 nM to 1 μM. The resulting electrodes were washed twice with 2×SSC/0.1% SDS for 5 min, followed by 1 min of 0.2×SSC/0.1% SDS and 1 min of 0.1×SSC/0.1% SDS. Finally, the electrodes were briefly rinsed with $H_2O$ and dried with $N_2$. A DNA target concentration of 1 μM was selected because of the shorter time required to reach hybridization saturation.

DNA Covalent Labeling with Complex II

DNA target sequence (5'-H$_2$N—(CH$_2$)$_6$-CTGAACGG-TAGCATCTTGAC) at 10 μM concentration was combined with a 100-fold excess of II in 50 mM potassium phosphate (pH 7.0), in the presence of 0.10 M EDC and 0.24 M NHS at room temperature with overnight agitation. DNA target labeled with II was purified from the reaction mixture by passage through a size-exclusion oligoDNA mini-spin column twice and was used in hybridization reactions as described in the previous section.

DNA Covalent Labeling with Complex III

Double-strand hybridized DNA-modified ITO electrodes were immersed in an approximately 10$^{-4}$ M solution of III in dichloromethane for 1 hour. During this period, the intercalative association of the redox active indicator with duplexed DNA was believed to occur. The resulting electrodes were then rinsed with acetonitrile, soaked in dichloromethane for 1 hour in order to remove weakly interacting redox labels, rinsed thoroughly again with acetonitrile and dichloromethane and dried under nitrogen. The same procedure was applied to ssDNA-modified electrodes and to carboxylic acid-derivatized ITO surfaces in order to assess both complex stability and major affinity of the redox label for hybridized dsDNA.

Materials Characterization

Electrochemistry

Electrochemical studies were performed using a Bioanalytical System BAS 100 B Potentiostat-Galvanostat controlled by BAS 100 W software resident on an IBM-compatible personal computer. A standard three-electrode configuration was used for all electrochemical experiments. The counter electrode was a large area platinum flag and a sodium-saturated calomel electrode (SSCE) was used as the reference electrode. The working electrode was either an ITO electrode (modified or unmodified, vide supra) or a conventional electrode as specified. In all cases, 0.1M TBAPF$_6$ in acetonitrile was employed as a supporting electrolyte.

X-Ray Photoelectron Spectroscopy (XPS)

XPS studies of electrode surfaces performed in a Physical Electronics PH15800 spectrometer equipped with a concentric hemispherical analyzer and average pressure in the high vacuum chamber during analyses of approx. 5×10$^{-9}$ torr. Aluminum monochromatic K$_\alpha$ source radiation (1486.6 eV) was used and sample photoelectrons were collected at a 15° take-off angle (sampling depth 2 nm). Physical Electronics PC ACCESS and MULTIPAK resident software controlled data acquisition and processing. Full survey scans were performed using a pass energy of 187.85 eV with an eV/step of 0.800 and acquisition time of 4 minutes. Utility scans used a pass energy of 117.4 eV and eV/step of 0.5, acquiring core level C1s and N1s signals for 10 minutes. Finally, high-resolution N1s and C1s spectral acquisitions were performed employing 23.5 eV pass energy and 0.1 eV/step for 15 minutes. Voigt profile fitting of the XPS spectra was achieved by means of the XPS PEAK 4.1 program.

Results and Discussion

Immobilization of ssDNA Probe onto ITO Electrode Surfaces

Figure 4:
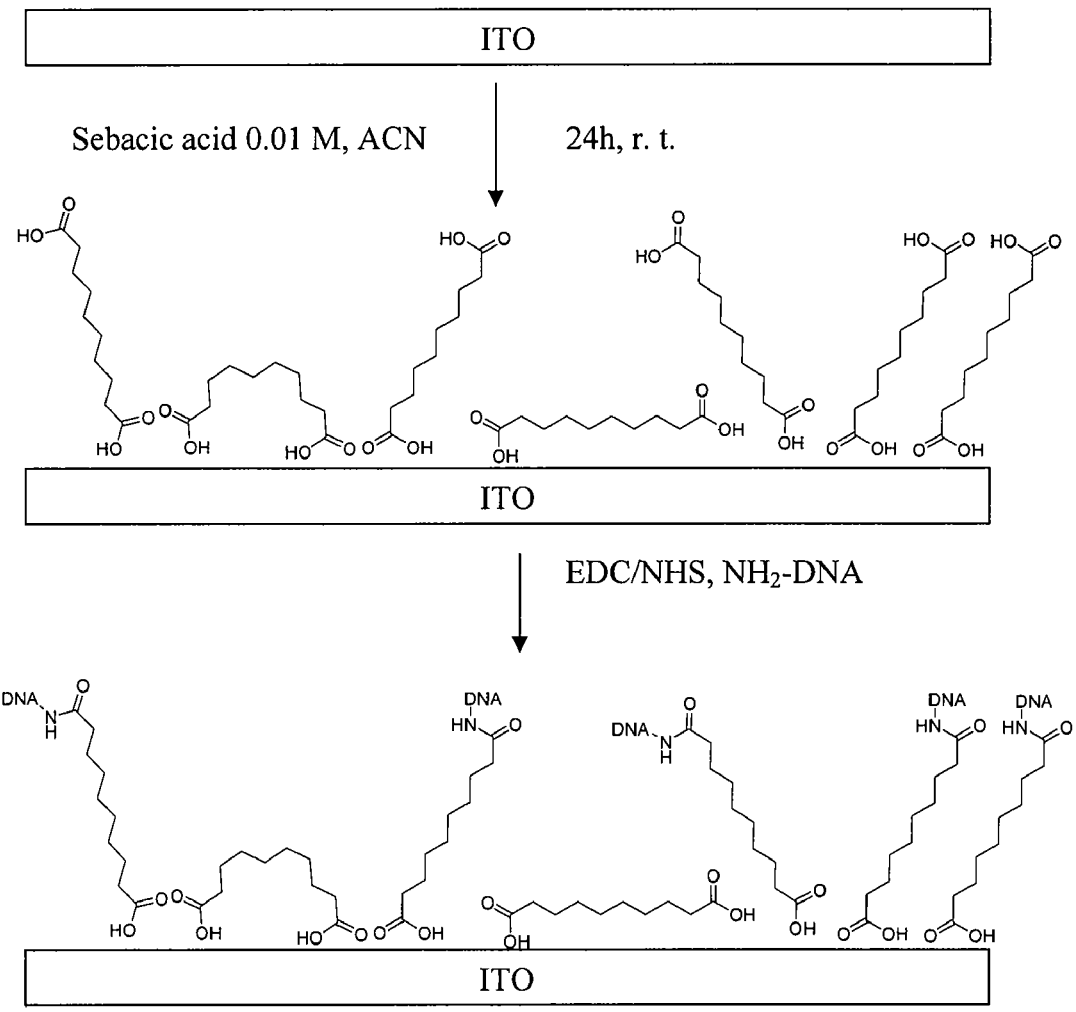
FIG. 4 illustrates a schematic attachment of oligonucleotides to carboxylic acid-modified ITO electrodes.

Many carboxylic acid-derivatized molecules readily form stable physisorbed monolayers on metal oxide surfaces, for example, the dicarboxylic acid, sebacic acid, can be used as an anchoring group for amino-modified oligonucleotides on ITO. Common carbodiimide-activated amide bond formation between alkanoic acid-coupled electrodes with amino-functionalized DNA bases are known, for example, polynucleotides can be attached to the carboxylic acids on oxidized glassy carbon surfaces or to aliphatic carboxylic acids (e.g. stearic acid) mixed into a carbon paste electrode. This procedure used to bind oligonucleotides to ITO substrates is represented schematically in FIG. 4.

DNA probe amino-terminated nucleotides were anchored onto a preformed sebacic acid monolayer using NHS and EDC for amidation. Direct mixing of NHS/EDC with DNA in a single step reliably produces similar surfaces. Unreacted NHS active esters, not consumed by DNA terminal alkylamines during immobilization, were rapidly consumed in hydrolysis reactions, leaving residual carboxylic acid groups at the surface.

XPS Surface Analysis

XPS provides substantial surface-sensitive analytical evidence for the successful step-by-step coupling reactions for the DNA binding to derivatized ITO electrodes (Gong et al., *Anal Chem.*, 2006, 78 (7), 2342-2351). One of the most significant signal is the N1s peak near 400 eV; within experimental error, nitrogen is in fact totally absent on the carboxylic acid-derivatized surface prior to DNA coupling and is introduced only after attachment of the oligoDNA, ostensibly due to the surface presence of the purine and pyrimidine DNA bases. Low abundance of phosphorus in DNA (4-5%) combined with its small photoelectron cross-section result in very poor phosphorus XPS signal.

Figure 6:
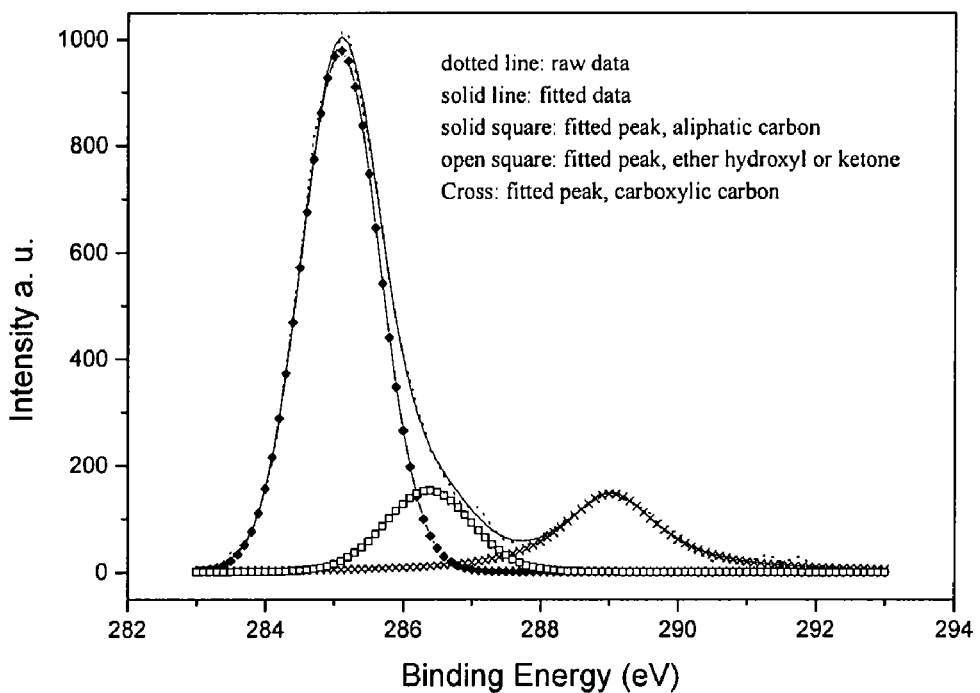
FIG. 6 is a XPS high-resolution core C1s photoelectron signal of sebacic acid-modified ITO surface with contributing peaks distinguishing several different carbon chemical species on the surface.

Fitting the high-resolution C1s photoelectron signal, centered at 285 eV, also provides further information about the presence of DNA on the electrode surface. From the spectral fits, contributions of carbon atoms in different chemical environments can be determined. FIG. 6 shows the C1s signal for sebacic acid on ITO, best fitted with three Gaussian-Lorentzian functions. The most intense peak, near 285.0 eV, is assigned to aliphatic carbon (—CH$_x$—), while the smaller peaks at higher binding energies (286.5 and 289.0 eV) originate from carbon atoms of ether, hydroxyl and ketone groups (open square) and carboxylic acid groups (crosses).

Figure 7:
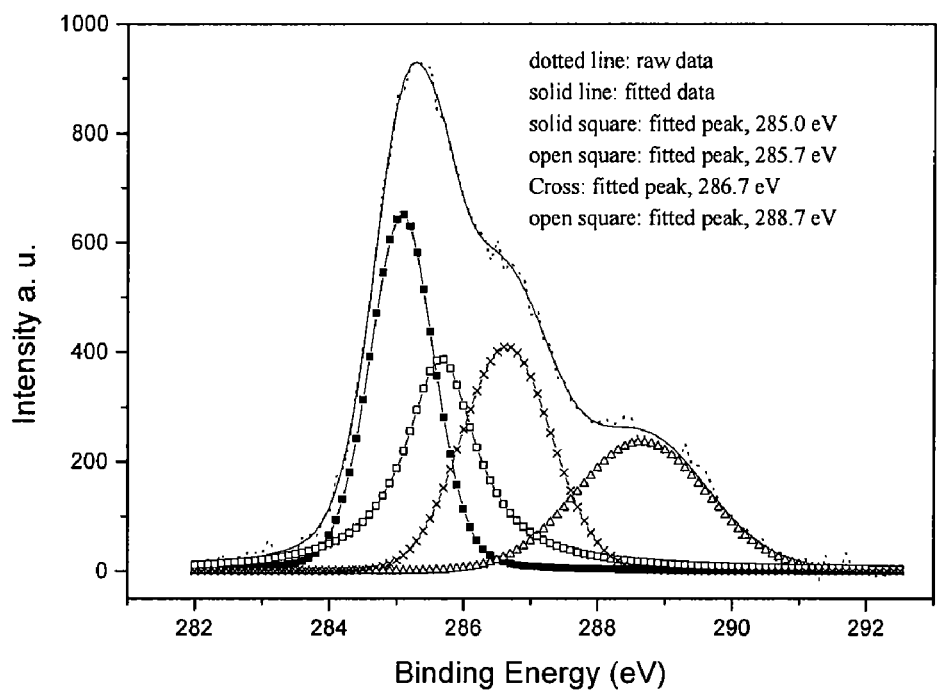
FIG. 7 is an XPS high-resolution C1s photoelectron signals from DNA-modified ITO surfaces. Oligonucleotides were attached to ITO using EDC/NHS coupling in water at pH 5.

After DNA attachment to ITO, both the survey (FIG. 8, "ITO-COOH" versus "ITO-COOH+EDC/NHS+NH$_2$-DNA") and high-resolution C1s signal (FIG. 6 versus FIG. 7) change dramatically. Post-attachment, the C1s high-resolution envelope is best fit with four Voigt profiles. As can be observed by comparing FIGS. 6 and 7, the relative intensities of the resulting photoelectron signals are completely changed. While precise assignment of each signal to particular carbon atoms cannot be certain due to the complexity of the DNA chemistry, the spectrum provides further evidence for presence of surface-bound oligonucleotides. Specifically, the appearance and increase in C1s peaks at binding energies greater than 285 eV arising from electron-deficient carbon atoms adjacent to electronegative atoms (e.g., nitrogen and oxygen) as one would expect from simple qualitative considerations of nucleotide chemical structures. Poor signal-noise prohibited similar analysis of N1s and P2p high-resolution peaks.

Figure 8:
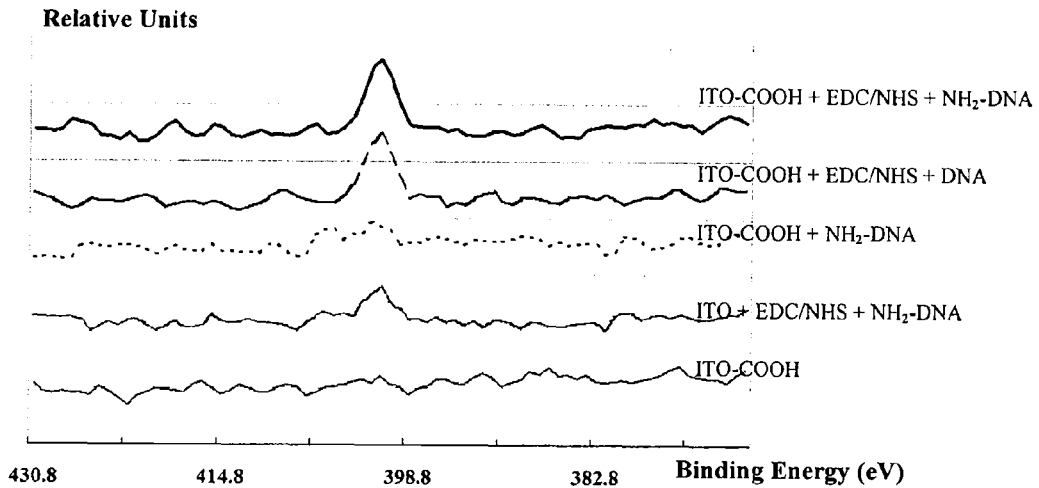
FIG. 8 is an XPS survey scans comparing immobilization of oligo-DNA on carboxylic acid-modified ITO with and without functional compatibility. Interaction of DNA with bare ITO without coupling reagents (negative control) is also examined. (15° takeoff angle).

While highest immobilized DNA surface concentrations as monitored by XPS were obtained using aminoalkyl-modified oligonucleotides and NHS/EDC coupling to carboxylic acid-derivatized surfaces, roughly comparable DNA quantities were also observed on ITO using control non-amino-modified oligonucleotides (FIG. 8). Amide bonds have been reported between carboxylic acids and DNA base exocyclic amines, despite the high pKa observed for these amino groups. Moreover, simple non-specific DNA binding cannot be excluded. FIG. 8 shows that without NHS/EDC coupling agents, amino-derivatized DNA does not interact significantly with the carboxylic acid-modified surface, while the control run on bare ITO using EDC/NHS coupling (but no sebacic acid), presence of measurable surface-bound DNA was observed. Nucleic acids have several non-specific modes of interaction with polar surfaces including metal oxides, from multiple hydrogen bonding to coordination of the polyphosphate backbone to hard $In^{3+}$ and $Sn^{4+}$ metal centers (Armistead et al., *Anal. Chem.*, 2000, 72(16), 3764-70). In summary, the XPS observation that the carboxylic acid layer hinders significant non-specific oligonucleotide interaction and binding with ITO was important and provides a basis to exclude the presence of physisorbed DNA not covalently bound to the surface of the electrochemical sensor.

A DNA probe surface density of $2 \times 10^{12}$ molecules/$cm^2$ was determined from radiometric measurement.

Figure 9:
FIG. 9 is surface fluorescence scans of an ITO electrode modified with cyanine dye-labeled oligonucleotide. The right circle was spotted with dye-labeled DNA with the EDC/NHS coupling agents and the left circle without the coupling agents.

Single-stranded DNA surface binding was also confirmed using fluorescence signal from a cyanine dye-labeled oligonucleotide under the same experimental conditions previously described for DNA attachment to modified ITO electrodes. The presence of surface-bound spotted DNA, as a homogeneous fluorescent region is clearly evident from FIG. 9. No fluorescence was obtained from the surface spotted with dye-labeled DNA without the EDC/NHS coupling agents.

Electrochemical Labels

Some of the desired characteristics of electrochemical labeling suitable for DNA detection are: (1) reversible or quasi-reversible electrochemical behavior on ITO electrodes with (2) a half-wave potential sufficiently positive to efficiently catalyze Co(II) oxidation, and (3) produce desired current amplification for signal enhancement. The redox potential, however, should not be too positive, preferably less than 800 mV vs SCE, in order to avoid the redox chemistry with the DNA itself, in particular the known oxidation of guanine near 1.0 V vs SSCE. In addition, the electrochemical label should have a selective or specific ability to bind covalently to DNA or interact with some degree of specificity with only dsDNA formed on the electrode after the target hybridization procedure. These collective requirements supported selection of the Ru(II) complexes whose structures are reported in FIG. 3.

Complex II was designed to bind covalently to DNA strands via amide bond formation between activated carboxylic acids and DNA terminal primary hexylamine groups, following the same strategy used for oligonucleotide surface attachment. Complex III was chosen for its ability to intercalate electrode-bound dsDNA via its phenothiazine groups. This was based on previous reports of phenothiazine derivatives exhibiting base pair intercalation through ☐ stacking interactions similar to many other planar aromatic molecules. (See, for example, Wang et al., *Analytica Chimica Acta*, 1996, 332, 139-144; Vanickova et al., *Chem. Anal.* (Warsaw), 2000, 45, 125; S. Yabuki et al., *Bioelectrochemistry*, 2004, 63, 253-255; J. Zhong et al., *Analytical Sciences*, 2003, 19(5), 653; A. Erdem et al., *Electroanalysis*, 2002, 14(14), 965). Such intercalation is believed to be much more selective for dsDNA than ssDNA due to mare stable insertion into stacked nucleotide bases in dsDNA. (Xu et al., *Electroanalysis*, 2006, 18(9), 873-881). In addition, being a zero charge (neutral) complex, III should avoid non-specific electrostatic interactions between the electroactive mediator and the nucleic acid.

Figure 10:
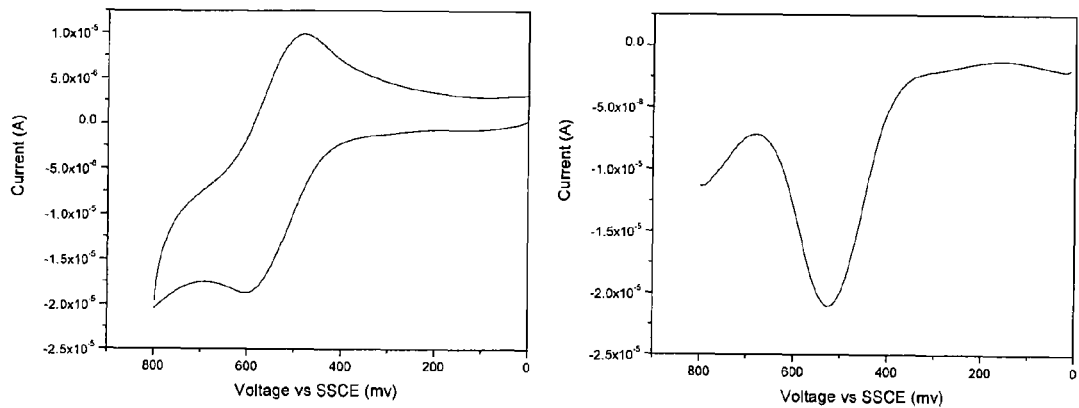
FIG. 10 is cyclic voltammetry (a) and differential pulsed voltammetry (b) for complex II recorded using an ITO working electrode in $MeOH/TBAPF_6$, (0.1M); scan speed 100 mV/s.
Figure 11:
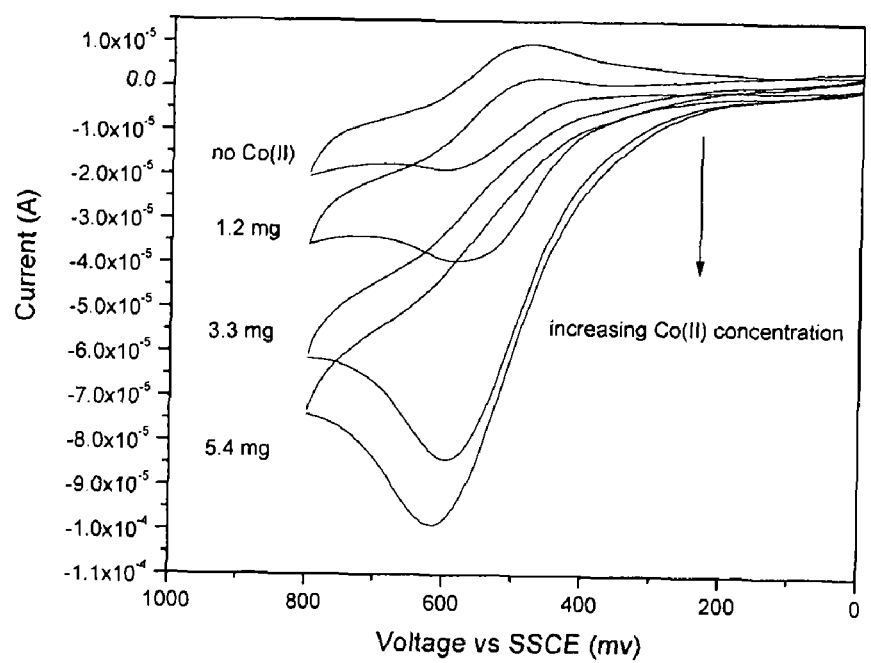
FIG. 11 is cyclic voltammetry of compound II in the presence of increasing complex I concentration, recorded using an ITO working electrode in $MeOH/TBAPF_6$ 0.1M, scan speed 100 mV/s.

Electrochemical behavior of these redox agents was initially studied in methanol and acetonitrile solution on ITO working electrodes using cyclic voltammetry (CV) and differential pulse voltammetry (DPV). The expected Co(II) catalytic oxidation promoted by these redox mediators was also investigated. Complex II gives rise to a one-electron, metal-centered, quasi-reversible oxidation wave characterized by a half-wave potential of 540 mV vs. SSCE and by a peak separation of 120 mV (see FIG. 10). The peak separation, substantially larger than in an ideal reversible case (60 mV), indicates a slower-than-diffusion-controlled heterogeneous electron transfer between the electro active species and the ITO surface. The $EL_{1/2}$ for the Co(II/III) couple in $Co(DTB)_3$ has been determined by cyclic voltammetry on working electrodes other than ITO to be ca. 150 mV vs SSCE—a value at least 350 mV negative of the $E_{1/2}$ for II (Sapp et al., *J. Am. Chem. Soc.*, 2002, 124 (37), 11215-11222). As observed in the cyclic voltammograms reported in FIG. 11, compound II catalyzes the oxidation of $Co(DTB)_3^{2+}$. The catalysis is as manifested by the increase in anodic wave intensity in the presence of increasing Co(II) concentrations and by the disappearance of a cathodic wave. The absence of a cathodic wave signifies that all Ru(III) electro-generated during the forward scan is reduced in solution by the $Co(DTB)_3^{2+}$ complex, and is therefore no longer available for re-reduction at the electrode.

Figure 12:
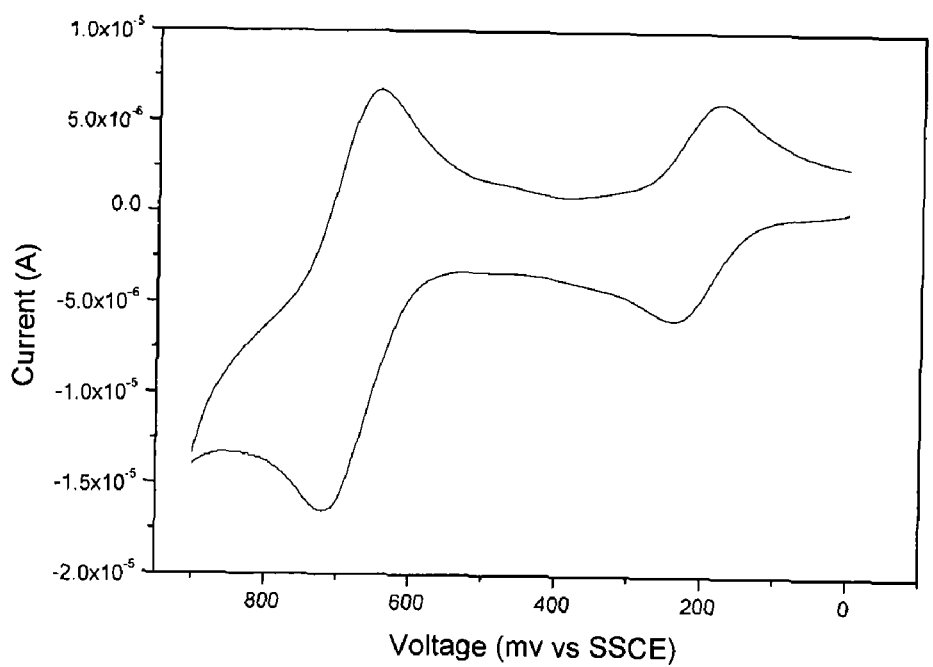
FIG. 12 is cyclic voltammetry of III recorded on an ITO working electrode in $ACN/TBAPF_6$ (0.1M); scan speed 100 mV/s.

The electrochemical behavior of compound III is more complex, as shown in FIG. 12. The reversible process at $E_{1/2}=208$ mV vs SSCE, is the one-electron metal-centered ruthenium oxidation. The second process, with an $E_{1/2}$ of ca. 700 mV results from the simultaneous one-electron oxidation of each of the two PTZ moieties (Larson et al., J. Phys. Chem. 1995, 99, 6530-6539).

Figure 13:
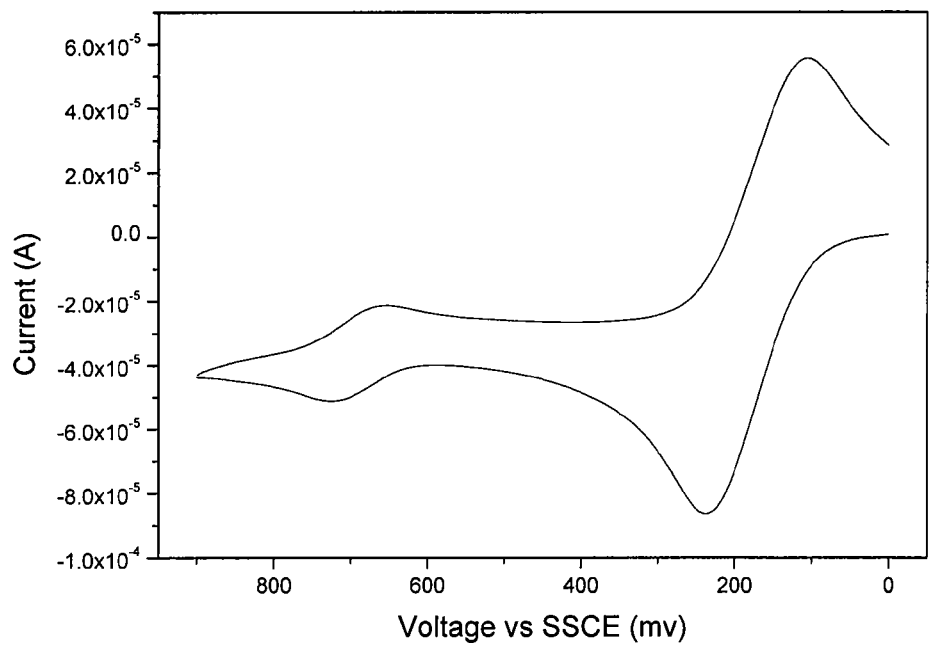
FIG. 13 is cyclic voltammetry of III in presence of complex I recorded using an ITO working electrode in $ACN/TBAPF_6$ (0.1M); scan speed 100 mV/s.

As with complex II, complex III also produces a large current amplification in presence of $Co(DTB)_3^{2+}$ (FIG. 13 versus FIG. 12); however, since the redox potentials of III and $Co(DTB)_3^{2+}$ are nearly coincidental, III can catalize the $Co(DTB)_3$ redox chemistry in either direction; thus the current is amplified for both the oxidation and reduction. The PTZ-centered oxidation was only marginally amplified, meaning that almost all Co(II) present in the diffusion layer was intercepted by the first electrode process, as displayed in FIG. 13.

Electrochemical Detection of DNA Target Hybridization

Figure 14A:
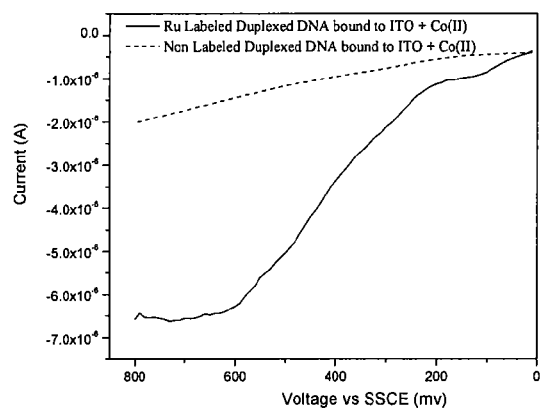
FIG. 14A is DPV of II-labeled dsDNA (solid line) compared with non-labeled duplexed dsDNA. (dashed line).
Figure 14B:
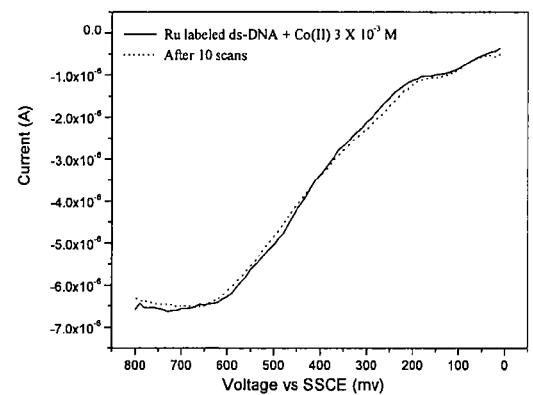
FIG. 14B the same electrode as FIG. 14A during the first (solid line) and tenth (dotted line) potential sweeps. Voltammetry recorded in $ACN/TBAPF_6$ (0.1M) in presence of $3\times10^{-3}$ M [Co(II)], scan speed 50 mV/s, potential pulse=50 mV.

Hybridization events of the immobilized DNA probe with the III-labeled DNA complementary targets were revealed by differential pulse voltammetry in presence of $3 \times 10^{-3}$M Co(II) in acetonitrile. As seen from the voltammograms recorded in FIG. 14A, the current arising from the Ru-labeled DN (solid line) was much larger if compared to a non-labeled dsDNA hybridized electrode (dashed line). The lack of a diffusion-limited shaped peak, and rough plateau in the differential current positive of 600 mV suggests kinetic control of one of the steps in the electrode process: specifically, either the rate of Co(II) oxidation by the oxidized ruthenium label or the rate of the oxidation of the ruthenium label by the electrode. The hybridized DNA surface concentration (and consequently, the Ru label concentration) was on the order of picomoles/$cm^2$—at least one order of magnitude less than the estimated value for a close-packed monolayer of II. Moreover, access to the ruthenium site by the $Co(DTB)_3^{2+}$, to some degree, may be hampered by the DNA structure. Each factor could serve to limit the rate of Ru(III)/Co(II) electron transfer. The rate of Ru(II)/ITO electron transfer could be limited by weak coupling through the surface-attached DNA. Hybridization of the DNA was shown by these standard electrochemical techniques and distinguished from ssDNA and non-labeled dsDNA controls. Finally, these results were reproducible, giving similar responses on several different electrodes without showing any decrease in response even after repeated potential sweeps (FIG. 14B).

Figure 15A:
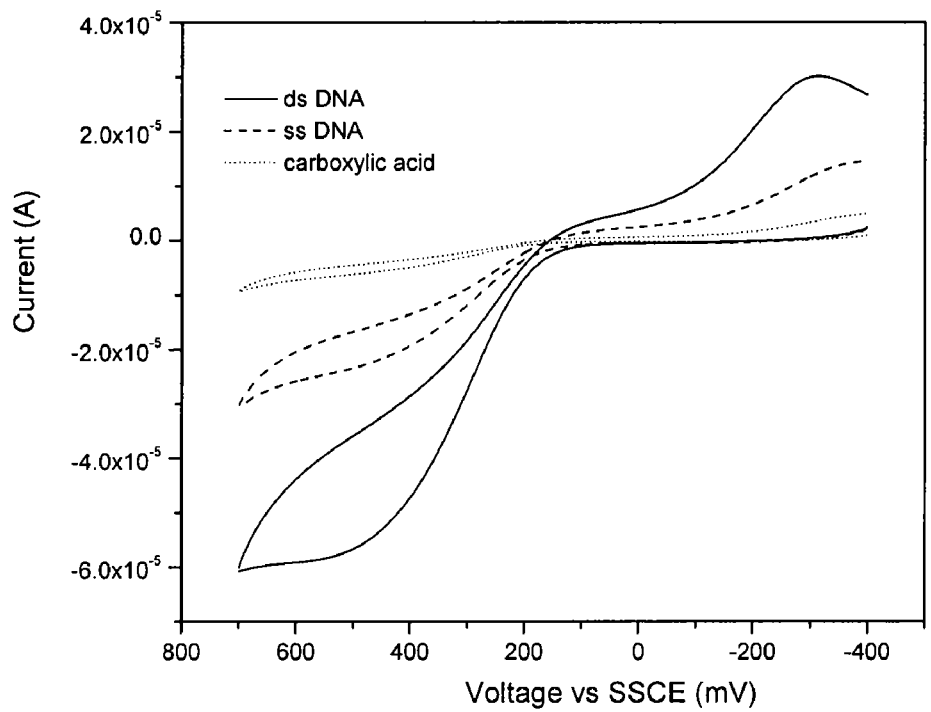
FIG. 15A is the cyclic voltammetry of III-labeled dsDNA (solid line) compared with III-labeled ssDNA and III-labeled sebacic acid
Figure 15B:
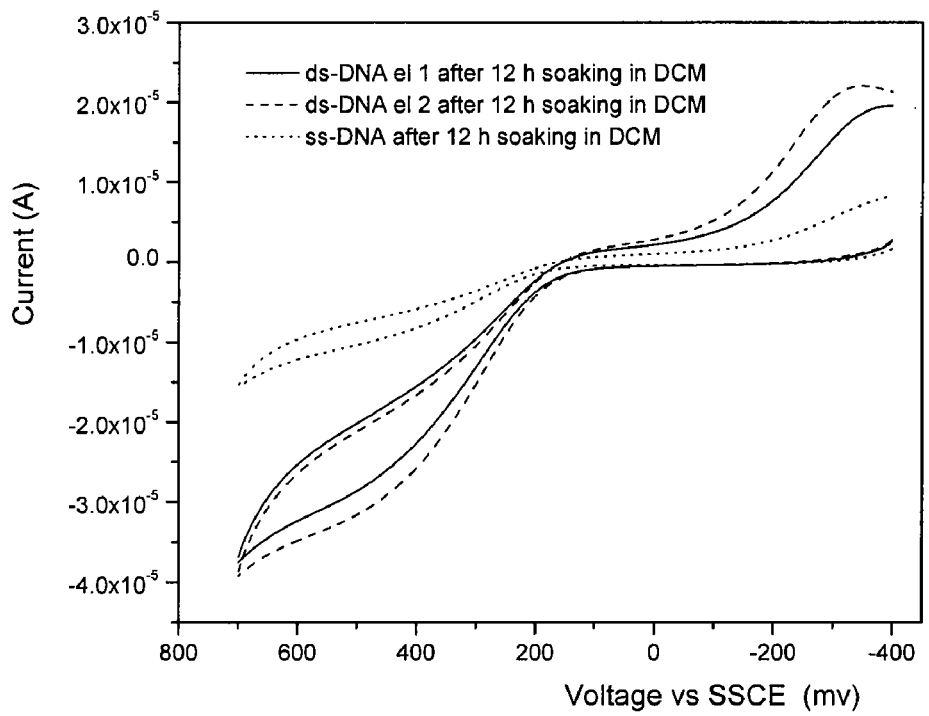
FIG. 15B is the cyclic voltammetries of two III-labeled dsDNA (solid line and dashed line) and one III-labeled ssDNA (dotted line). All the electrodes were soaked in dichloromethane for 12 hs after III treatment.

Results were also obtained with the intercalative redox label III as shown in the cyclic voltammograms in FIG. 15A. ITO electrodes modified with ssDNA alone and modified with ssDNA which was subsequently hybridized with its complement from solution were each challenged with solutions of III. After soaking these electrodes in pure solvent to remove physisorbed III, the electrodes were placed into a solution containing $Co(DTB)_3^{2+}$ and their potential cycled. The electrodes modified with the dsDNA gave rise to catalytic currents that were from 5 to 7 times larger than for the ssDNA. The higher current results from a more effective Co(II) catalytic oxidation, which can be rationalized by a larger surface concentration of intercalated Ru complex on the dsDNA modified surface. The sigmoidal shape of the CVs and the absence of a well-defined diffusional-shaped peak is indicative of kinetic control over the overall redox process. In any case, the absolute value of the peak current, approximating 60 µA, allows for a simple and quick detection of hybridization. The stability of the association between the dsDNA and the redox marker is demonstrated by the CVs reported in FIG. 15B. After 12 hours of soaking the electrodes in dichloromethane, dsDNA was still possible to distinguish from ssDNA, despite an overall decrease in absolute current intensity: the ratio between current obtained from the intercalated dsDNA and the intercalated ssDNA was in fact substantially unchanged. That the complex also binds to ssDNA oligonucleotide was not surprising given that some degree of π stacking was known to occur even in non-duplexed DNA fragments (Zhou et al., J. Chem. Physics, 2001, 114(19), 8694), in addition to other non-specific hydrophobic/van der Waals interactions.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for determining the presence or absence of a target substrate in a test sample comprising:
providing an electrode comprising:
a conductive surface, and
a probe that is bound to the conductive surface and is capable of binding to a target substrate;
contacting the conductive-surface bound probe with the test sample to form a surface bound target complex if the target substrate is present in the test sample, wherein the surface bound target complex further comprises a redox-catalyst complex that is capable of catalyzing an oxidation-reduction reaction;
contacting the surface bound probe or the surface bound target complex, if present, with a fluid medium comprising a redox transition metal complex that is capable of undergoing an oxidation-reduction reaction when the surface bound target complex comprising the redox-catalyst complex is present;
detecting the oxidation-reduction reaction of the redox transition metal complex that is at least in part catalyzed by the redox-catalyst complex; and
determining the presence or absence of the target substrate in the test sample from the detected oxidation-reduction reaction.

2. The method of claim 1, wherein the redox-catalyst complex is covalently attached to the target substrate.

3. The method of claim 1, wherein the electrode is contacted with the redox-catalyst complex after said step of contacting the conductive-surface bound probe with the test sample such that when the surface bound target complex is present, at least a portion of the redox-catalyst complex intercalates into the surface bound target complex.

4. The method of claim 1, wherein the redox transition metal complex is of the formula:

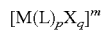

wherein
m is an integer;
p is an integer from 1 to 6;
q is an integer from 0 to 5;
provided that the sum of p+q is such that M has no more than six binding sites;
M is a transition metal that can exist in at least two stable oxidation sates within the transition metal complex;
each X is a ligand independently selected from the group consisting of a halide, cyanide, pyridine and amine; and
each L is independently an optionally substituted aromatic ligand that comprises one, two or three coordinating atoms each of which is independently selected from the group consisting of nitrogen, oxygen, and phosphorous.

5. The method of claim 4, wherein each L is independently selected from the group consisting of bipyridine, terpyridine, and phenanthroline, each of which is optionally substituted.

6. The method of claim 4, wherein M is Co.

7. The method of claim 4, wherein at least one of the aromatic ligand is substituted with a substituent having a steric bulk volume larger than a methyl group.

8. The method of claim 7, wherein each L is independently selected from the group consisting of:

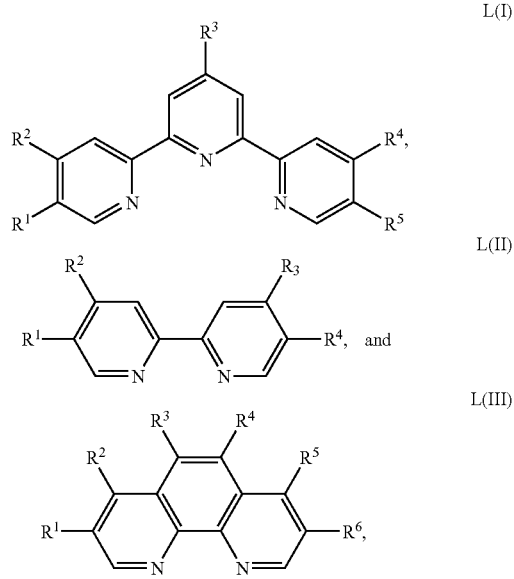

wherein
each of $R^1$, $R^2$, $R^3$, $R^4$, $R^5$, and $R^6$ is independently hydrogen, alkyl, cycloalkyl, aryl, aralkyl, an ester moiety of the formula —$CO_2R^7$, an amide moiety of the formula —$CONR^8R^9$;
$R^7$ is alkyl, cycloalkyl, aryl, or aralkyl; and
each of $R^8$ and $R^9$ is independently hydrogen, alkyl, cycloalkyl, aryl, or aralkyl; provided at least one of $R^1$, $R^2$, $R^3$, $R^4$, or $R^5$ in L(I), or at least one of $R^1$, $R^2$, $R^3$, or $R^4$ in L(II), or at least one of $R^1$, $R^2$, $R^3$, $R^4$, $R^5$, or $R^6$ in L(III) is a substituent having a steric bulk volume larger than a methyl group.

9. The method of claim 8, wherein the redox transition metal complex is of the formula: $[M(L(I))_2]^{+m}$, $[M(L(II))_3]^{+m}$, or $[M(L(III))_2]^{+m}$, wherein M and m are those defined in claim 4.

10. The method of claim 1, wherein the redox-catalyst complex is of the formula:

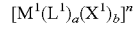     II wherein
n is an integer;
a is an integer from 1 to 6;
b is an integer from 0 to 5;
provided that the sum of a+b is such that $M^1$ has no more than six binding sites;
$M^1$ is a transition metal that can exist in at least two stable oxidation sates within the transition metal complex;
each $X^1$ is a ligand independently selected from the group consisting of a halide, cyanide, pyridine and amine; and
each $L^1$ is independently an optionally substituted aromatic ligand that comprises one, two or three coordinating atoms each of which is independently selected from the group consisting of nitrogen, oxygen, and phosphorous, and wherein at least one of the aromatic ligand comprises a linker that is attached to a binding moiety that is capable of binding to a double stranded oligonucleotide.

11. The method of claim 10, wherein $M^1$ is Ru, Fe, or Os.

12. The method of claim 10, wherein at least one of $L^1$ is of the formula:

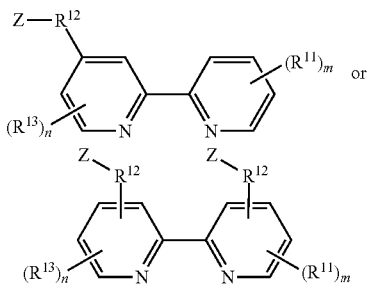

wherein
each m is independently an integer from 0 to 4;
each n is independently an integer from 0 to 3;
each of $R^{11}$ and $R^{13}$ is independently alkyl, or aryl;
each $R^{12}$ is independently $C_1$-$C_{12}$ alkylene; and
each Z is an intercalating moiety that is capable of intercalating into a double stranded oligonucleotide.

13. The method of claim 12, wherein m is 1.

14. The method of claim 12, wherein $R^{11}$ is methyl.

15. The method of claim 12, wherein m is 1.

16. The method of claim 12, wherein n is 0.

17. The method of claim 10, wherein the redox-catalyst complex is selected from the group consisting of $Ru(dppz)_2Cl_2$, $Ru(dmb)(dpphz)Cl_2$, $Os(dppz)_2Cl_2$, $Os(bpy)(dpphz)Cl_2$, $Os(dpphz)(phen)Cl_2$, $Os(dpdphphz)(phen)Cl_2$, $[Os(phen)(dpphz)(py)Cl]PF_6$, and $[Os(bpy)(dpdphphz)(py)Cl]PF_6$.

* * * * *